(12) United States Patent
Goldfarb et al.

(10) Patent No.: US 9,554,817 B2
(45) Date of Patent: Jan. 31, 2017

(54) MEDICAL DEVICE AND METHOD FOR TREATMENT OF A SINUS OPENING

(75) Inventors: Eric A. Goldfarb, Belmont, CA (US); Richard R. Newhauser, Jr., Redwood City, CA (US); Thomas R. Jenkins, Alameda, CA (US); John W. White, San Francisco, CA (US); Mina W. B. Chow, Campbell, CA (US); Serena Swei Loh, San Carlos, CA (US); Mei Y. Pader, Fremont, CA (US); Scott O. Chamness, Menlo Park, CA (US); Luke W. Clauson, Redwood City, CA (US); Matthew B. Newell, Redwood City, CA (US); Arthur M. Lin, Fremont, CA (US)

(73) Assignee: Acclarent, Inc., Irvine, CA (US)

( * ) Notice: Subject to any disclaimer, the term of this patent is extended or adjusted under 35 U.S.C. 154(b) by 1122 days.

(21) Appl. No.: 13/222,353

(22) Filed: Aug. 31, 2011

(65) Prior Publication Data
US 2012/0071856 A1 Mar. 22, 2012

Related U.S. Application Data

(60) Provisional application No. 61/385,250, filed on Sep. 22, 2010, provisional application No. 61/385,263, (Continued)

(51) Int. Cl.
*A61B 17/00* (2006.01)
*A61B 17/24* (2006.01)
(Continued)

(52) U.S. Cl.
CPC ........... *A61B 17/24* (2013.01); *A61M 25/0113* (2013.01); *A61M 25/09041* (2013.01);
(Continued)

(58) Field of Classification Search
CPC ................ A61B 17/24; A61B 17/3207; A61B 2017/00331; A61B 2017/22042; A61B 2017/22069; A61M 2025/09125; A61M 25/0113; A61M 25/09041
(Continued)

(56) References Cited

U.S. PATENT DOCUMENTS 4,509,945 A * 4/1985 Kramann ........... A61M 25/0111
600/434
4,757,827 A * 7/1988 Buchbinder et al. ......... 600/585
(Continued)

FOREIGN PATENT DOCUMENTS

CN 2458991 Y 11/2001
CN 101553190 A 10/2009
(Continued)

OTHER PUBLICATIONS

International Search Report re: PCT/US2011/049919 dated Nov. 16, 2011.

*Primary Examiner* — Kevin C Sirmons
*Assistant Examiner* — William Carpenter

(57) ABSTRACT

A medical device and method for the treatment of a sinus opening includes a handle, a guide catheter, a guide wire, a balloon catheter, a guide wire movement mechanism and a balloon catheter movement mechanism. The guide wire and balloon catheter are both disposed at least partially in the handle and catheter lumen. The guide wire movement mechanism is configured for advancement and retraction of the guide wire through the handle and catheter lumen by user operation of the guide wire movement mechanism. The guide wire movement mechanism includes an integrated guide wire locking and rotation mechanism configured for rotation of the guide wire and for securely locking and unlocking the guide wire to the guide wire movement mechanism. The balloon catheter movement mechanism is
(Continued)

configured for advancement and retraction of the balloon catheter through the handle and catheter lumen by user operation of the balloon catheter movement mechanism.

22 Claims, 33 Drawing Sheets

Related U.S. Application Data filed on Sep. 22, 2010, provisional application No. 61/511,237, filed on Jul. 25, 2011.

(51) Int. Cl.
*A61M 25/01* (2006.01)
*A61M 25/09* (2006.01)
A61B 17/3207 (2006.01)
A61B 17/22 (2006.01)
A61M 29/02 (2006.01)
A61M 25/06 (2006.01)

(52) U.S. Cl.
CPC . *A61B 17/3207* (2013.01); *A61B 2017/00292* (2013.01); *A61B 2017/00331* (2013.01); *A61B 2017/00535* (2013.01); *A61B 2017/22042* (2013.01); *A61B 2017/22069* (2013.01); *A61M 29/02* (2013.01); *A61M 2025/0681* (2013.01); *A61M 2025/09125* (2013.01)

(58) Field of Classification Search
USPC ..... 606/196, 199, 191, 185, 198; 604/96.01, 604/514, 509; 600/104
See application file for complete search history.

(56) References Cited

U.S. PATENT DOCUMENTS

| | | | |
|---|---|---|---|
| 5,460,185 A | 10/1995 | Johnson et al. | |
| 5,755,695 A * | 5/1998 | Erickson et al. | 604/164.13 |
| 6,752,800 B1 * | 6/2004 | Winston et al. | 604/528 |
| 7,462,175 B2 | 12/2008 | Chang et al. | |
| 7,500,971 B2 | 3/2009 | Chang et al. | |
| 7,645,272 B2 | 1/2010 | Chang et al. | |
| 7,654,997 B2 | 2/2010 | Makower et al. | |
| 7,803,150 B2 | 9/2010 | Chang et al. | |
| 8,834,513 B2 * | 9/2014 | Hanson | A61B 17/24 606/191 |
| 2002/0077594 A1 | 6/2002 | Chien et al. | |
| 2006/0063973 A1 * | 3/2006 | Makower et al. | 600/114 |
| 2006/0210605 A1 * | 9/2006 | Chang et al. | 424/434 |
| 2007/0167682 A1 * | 7/2007 | Goldfarb et al. | 600/114 |
| 2007/0208301 A1 | 9/2007 | Evard et al. | |
| 2008/0015544 A1 * | 1/2008 | Keith et al. | 604/516 |
| 2008/0082045 A1 * | 4/2008 | Goldfarb et al. | 604/96.01 |
| 2008/0097154 A1 | 4/2008 | Makower et al. | |
| 2008/0281156 A1 | 11/2008 | Makower et al. | |
| 2009/0030274 A1 * | 1/2009 | Goldfarb et al. | 600/106 |
| 2009/0287203 A1 | 11/2009 | Mazzone et al. | |
| 2010/0030113 A1 * | 2/2010 | Morriss | A61B 1/233 600/585 |
| 2010/0099946 A1 * | 4/2010 | Jenkins | A61B 1/0014 600/104 |
| 2010/0168511 A1 | 7/2010 | Muni et al. | |
| 2010/0312101 A1 * | 12/2010 | Drontle | A61B 17/24 600/424 |
| 2011/0288477 A1 * | 11/2011 | Ressemann et al. | 604/95.04 |

FOREIGN PATENT DOCUMENTS

| | | |
|---|---|---|
| CN | 201356607 Y | 12/2009 |
| DE | 102008022332 A1 | 11/2009 |
| EP | 2618886 B1 | 10/2015 |
| JP | 2005-529649 A | 10/2005 |
| WO | WO 00/38776 | 7/2000 |
| WO | WO 2008/000065 A1 | 1/2008 |
| WO | WO 2008/031103 | 3/2008 |
| WO | WO 2010/014799 A1 | 2/2010 |
| WO | WO 2010/033629 A1 | 3/2010 |

* cited by examiner

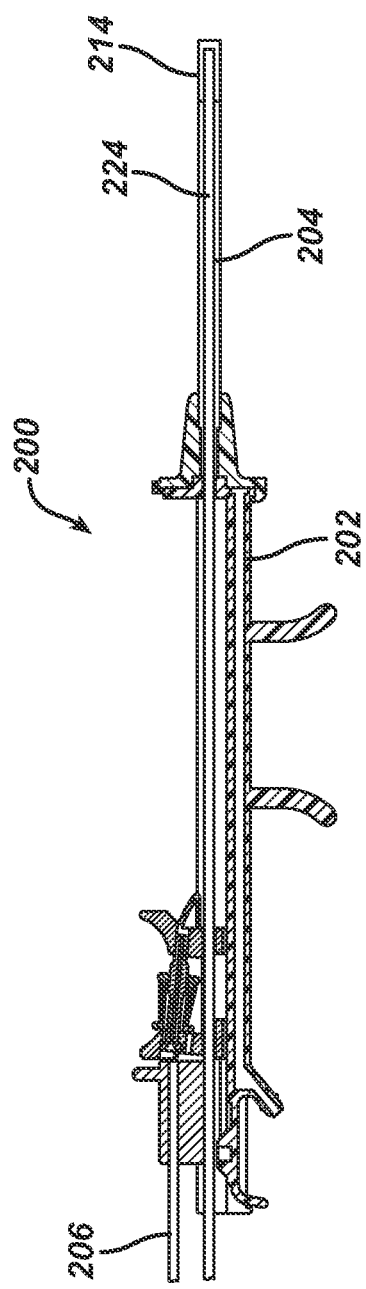

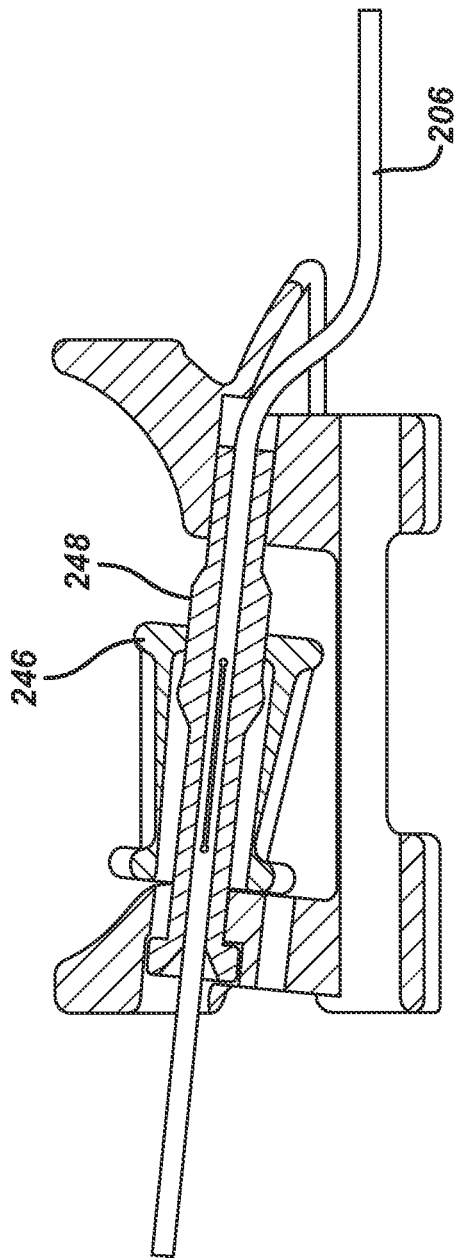

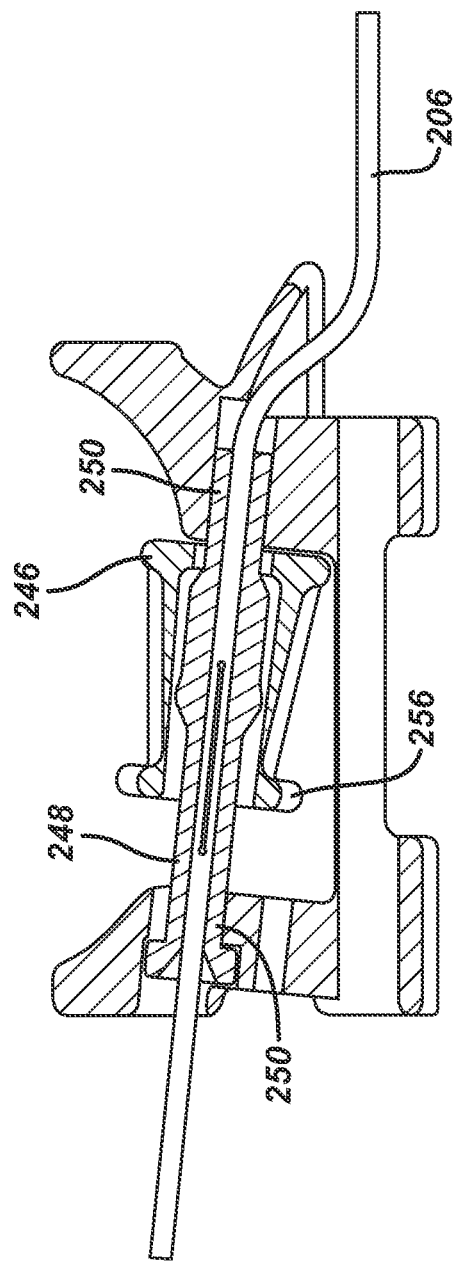

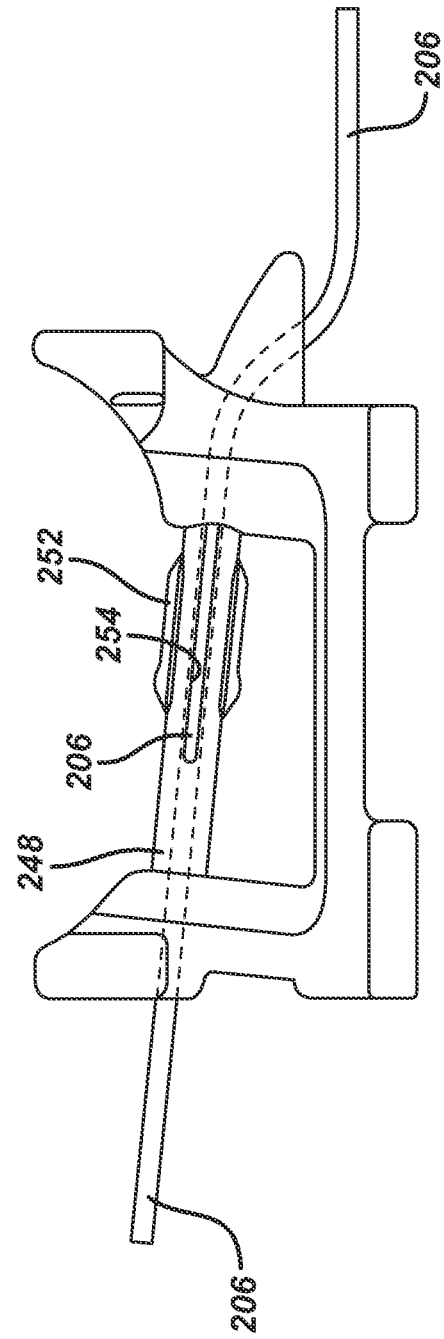

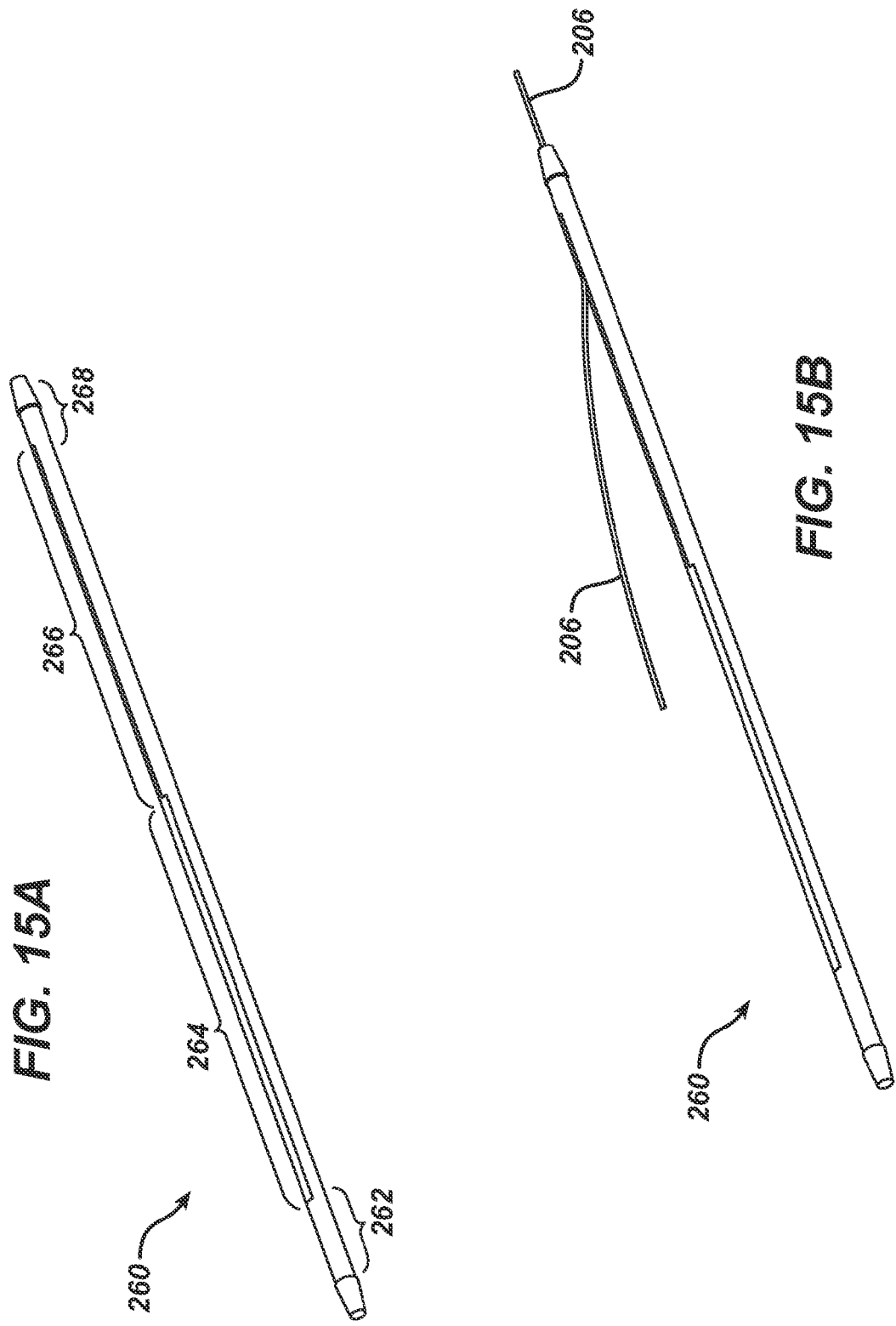

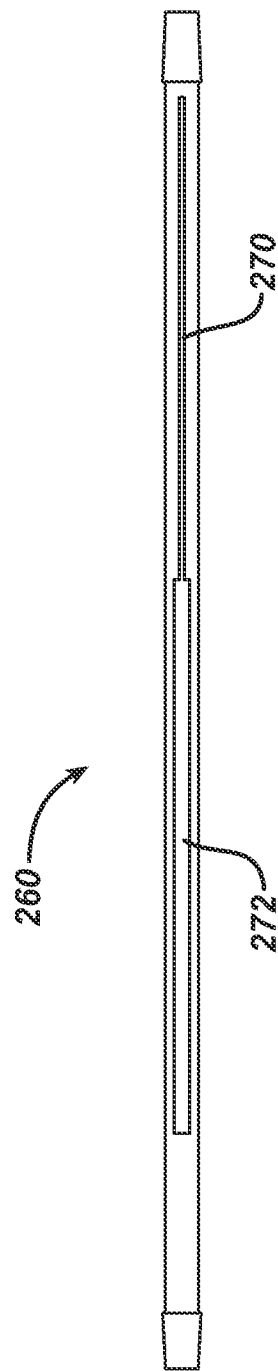

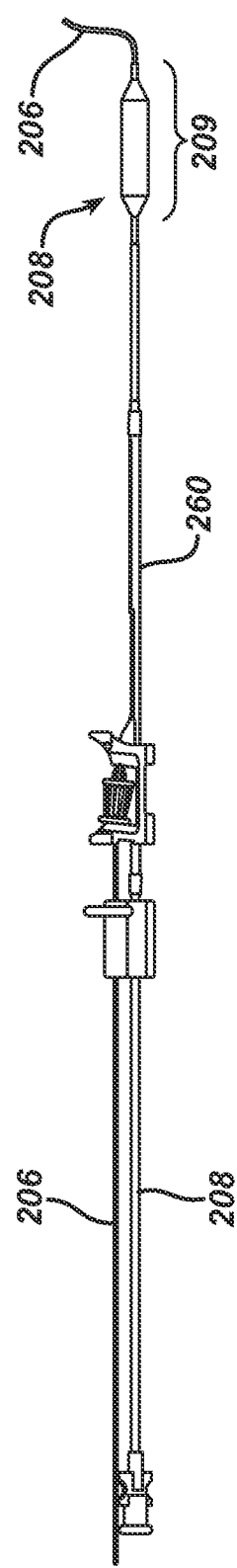

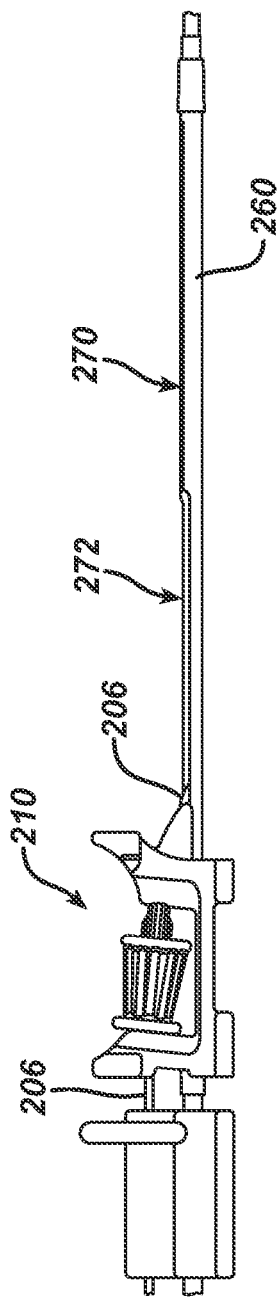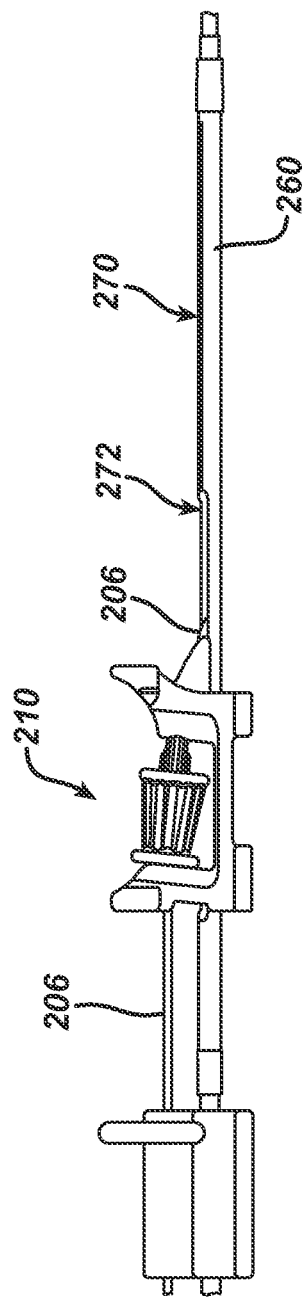

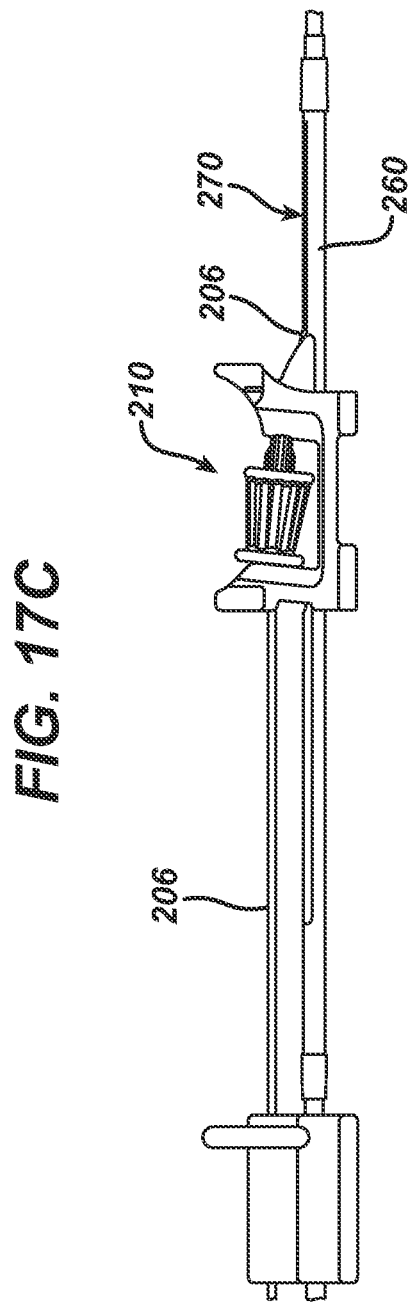

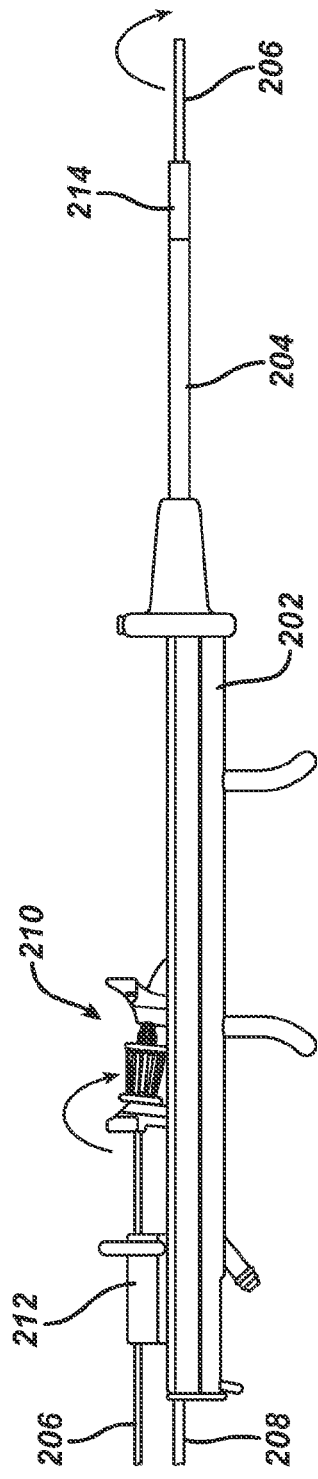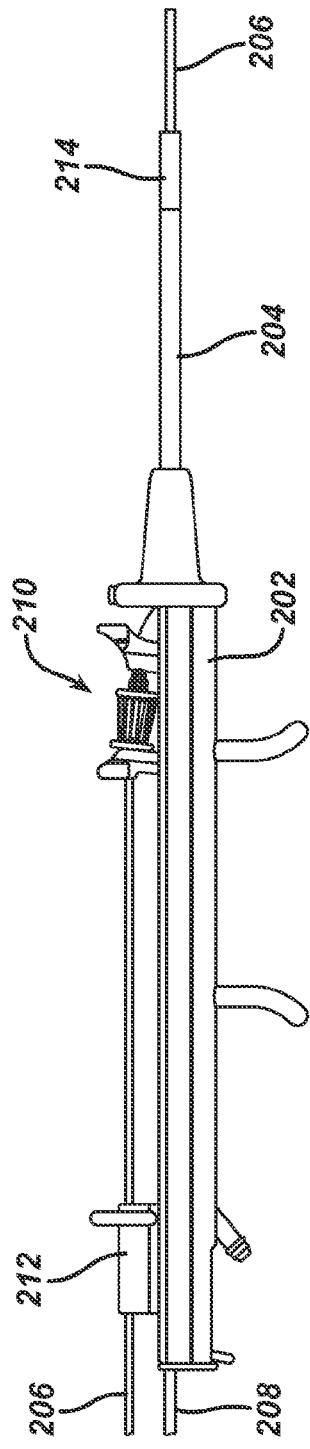

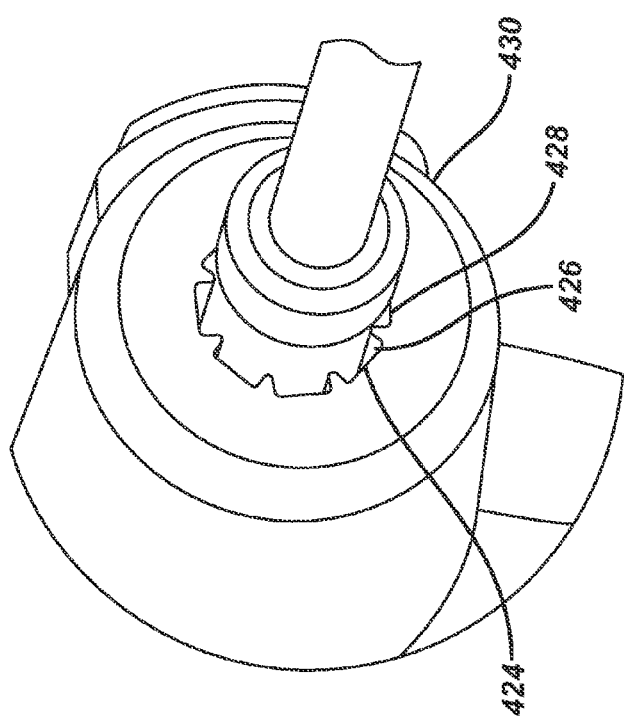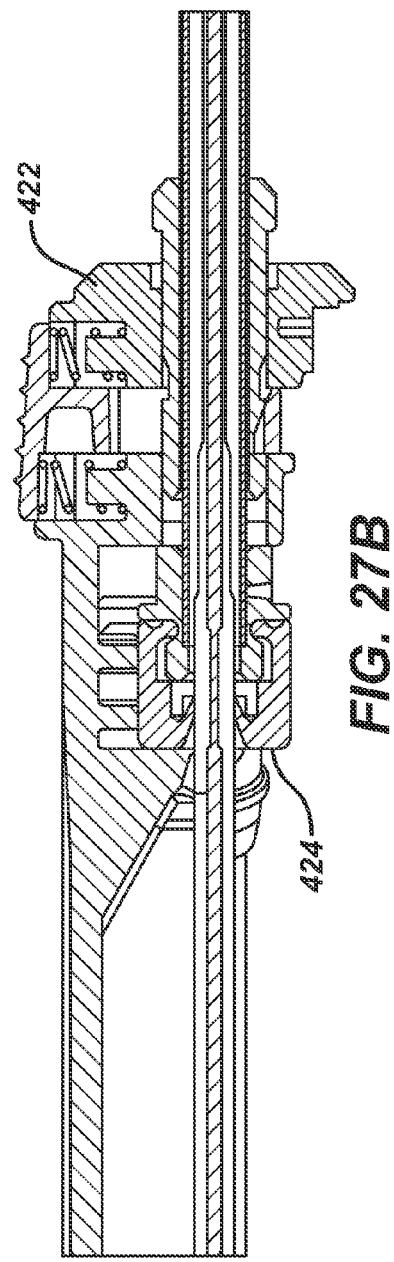

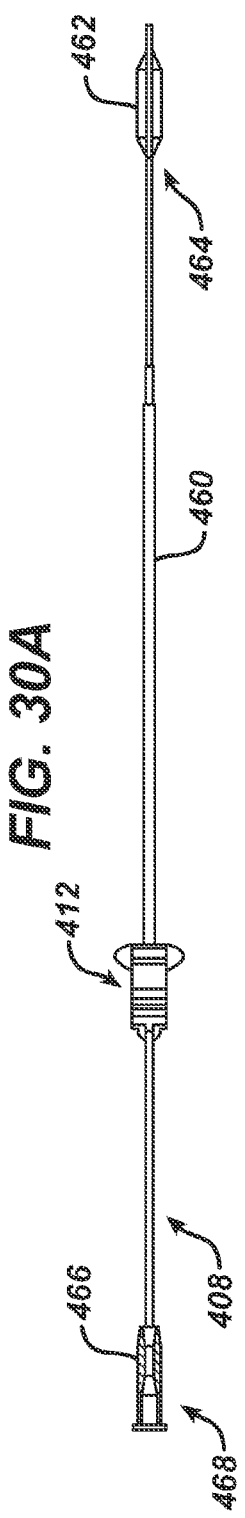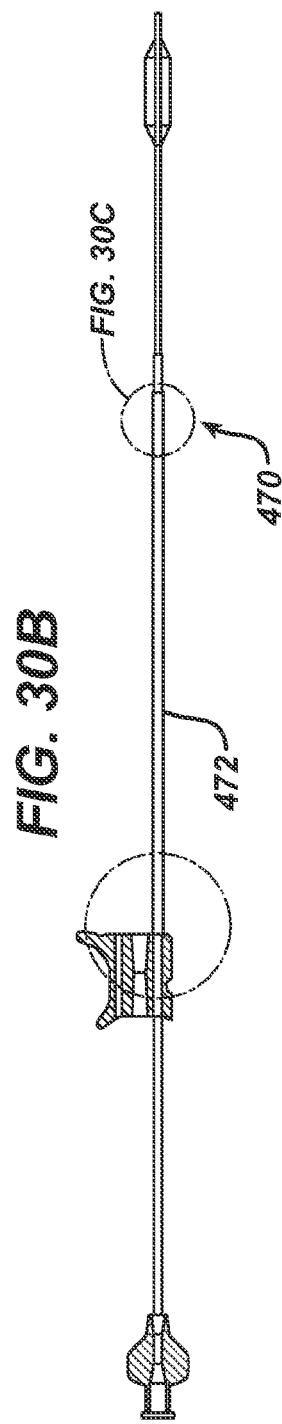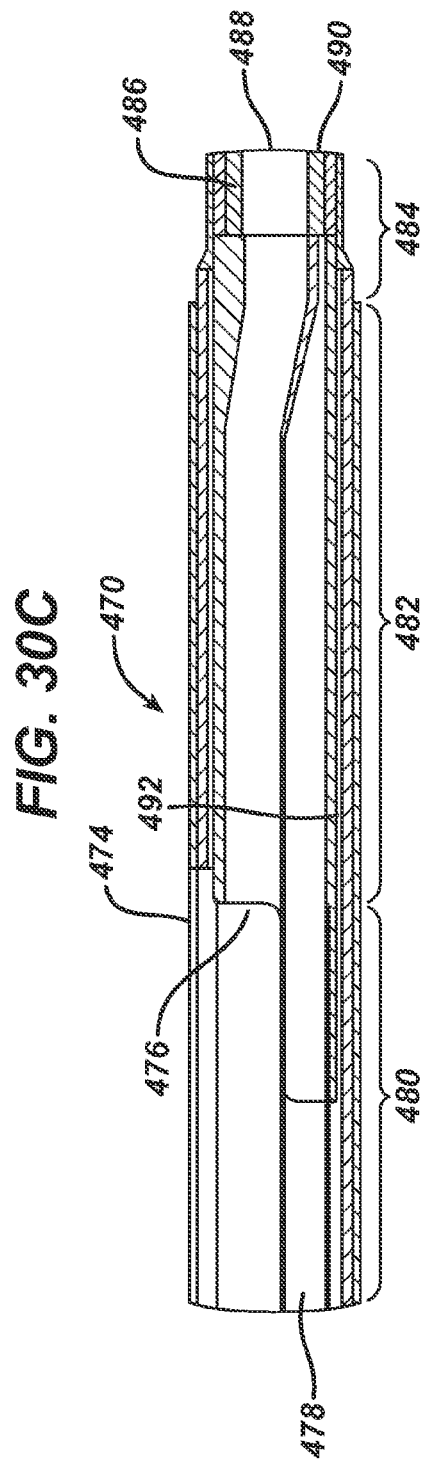

MEDICAL DEVICE AND METHOD FOR TREATMENT OF A SINUS OPENING

RELATED APPLICATIONS

This application claims priority pursuant to 35 U.S.C. §119 to U.S. Provisional Patent Application Ser. No. 61/385,250, entitled "Medical Device for Treatment of a Sinus Opening" filed on Sep. 22, 2010, U.S. Provisional Patent Application Ser. No. 61/385,263, entitled "Method for Treating a Sinus Opening" filed on Sep. 22, 2010 and U.S. Provisional Patent Application Ser. No. 61/511,237, entitled "Medical Device and Method for Treatment of a Sinus Opening" filed on Jul. 25, 2011, the entirety of these applications being incorporated herein by reference thereto.

FIELD OF THE INVENTION

The present invention relates, in general, to medical devices and, in particular, to medical devices and related methods for the treatment of sinus conditions.

BACKGROUND OF THE INVENTION

The paranasal sinuses are hollow cavities in the skull connected by small openings, known as ostia, to the nasal canal. Each ostium between a paranasal sinus and the nasal cavity is formed by a bone covered by a layer of mucosal tissue. Normally, air passes into and out of the paranasal sinuses through the ostia. Also, mucus is continually formed by the mucosal lining of the sinuses and drains through the ostia and into the nasal canal.

Sinusitis is a general term that refers to inflammation in one or more of the paranasal sinuses. Acute sinusitis can be associated with upper respiratory infections or allergic conditions, which may cause tissue swelling and temporarily impede normal trans-ostial drainage and ventilation of the sinuses, thereby resulting in some collection of mucus and possibly infection within the sinus cavities. Chronic sinusitis is a long term condition characterized by persistent narrowing or blockage of one or more sinus ostia, resulting in chronic infection and inflammation of the sinuses. Chronic sinusitis is often associated with longstanding respiratory allergies, nasal polyps, hypertrophic nasal turbinates and/or deviated internasal septum. While acute sinusitis is typically caused by infection with a single pathogen (e.g., one type of bacteria, one type of virus, one type of fungus, etc.), chronic sinusitis is often associated with multiple pathogen infections (e.g., more than one type of bacteria or more than one genus of micro-organism).

Chronic sinusitis, if left untreated, can result in irreparable damage to the tissues and/or bony structures of the paranasal anatomy. The initial treatment of chronic sinusitis usually involves the use of drugs such as decongestants, steroid nasal sprays and antibiotics (if the infection is bacterial). In cases where drug treatment alone fails to provide permanent relief, surgical intervention may be indicated.

The most common surgical procedure for treating chronic sinusitis is functional endoscopic sinus surgery (FESS). FESS is commonly performed using an endoscope and various rigid instruments inserted through the patient's nostril. The endoscope is used to visualize the positioning and use of various rigid instruments used for removing tissue from the nasal cavity and sinus ostia in an attempt to improve sinus drainage.

A technique known as the Balloon Sinuplasty™ procedure and a system for performing the procedure have been developed by Acclarent Inc, of Menlo Park, Calif. for treatment of sinusitis. A number of US patents and patent applications including U.S. Pat. Nos. 7,645,272, 7,654,997, and 7,803,150 and Publications 2008/0097154 and 2008/0281156 each of which is hereby incorporated in full by reference, describe various embodiments of the Balloon Sinuplasty™ procedure as well as various devices useable in the performance of such procedure. In the Balloon Sinuplasty™ procedure, a guide catheter is inserted into the nose and positioned within or adjacent to the ostium of the affected paranasal sinus. A guidewire is then advanced through the guide catheter and into the affected paranasal sinus. Thereafter, a dilation catheter having an expandable dilator (e.g. an inflatable balloon) is advanced over the guidewire to a position where the dilator is positioned within the ostium of the affected paranasal sinus. The dilator is then expanded, causing dilation of the ostium and remodelling of bone adjacent to the ostium, without required incision of the mucosa or removal of any bone. The catheters and guidewire are then removed and the dilated ostium allows for improved drainage from and ventilation of the affected paranasal sinus. There is a continuing need for improved methods and devices for treating the paranasal sinus.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings, in which like numerals indicate like elements.

SUMMARY OF THE INVENTION

The present invention provides devices and methods for treating a sinus opening.

In one aspect, a medical device is provided for the treatment of a sinus opening. The medical device includes a handle with a proximal end, a distal end, and a longitudinal axis along the length of the handle. The device further includes a guide catheter attached to the distal end of the handle, the guide catheter having a catheter lumen. The medical device further includes a guide wire movement mechanism operatively disposed on the handle, and a balloon catheter movement mechanism operatively disposed on the handle. The handle and the catheter lumen are configured for operatively accepting a guide wire and a balloon catheter. The guide wire movement mechanism is configured for advancement and retraction of a guide wire disposed at least partially in the handle and the catheter lumen through the handle and the catheter lumen by user operation of the guide wire movement mechanism. The guide wire movement mechanism includes an integrated guide wire locking and rotation mechanism configured for rotation of the guide wire and for securely locking and unlocking the guide wire to the guide wire movement mechanism. The balloon catheter movement mechanism is configured for advancement and retraction of a balloon catheter disposed at least partially in the handle and in the catheter lumen through the handle and catheter lumen by user operation of the balloon catheter movement mechanism.

In one embodiment, the medical device may further include a guide wire disposed at least partially in the handle and catheter lumen and a balloon catheter disposed at least partially in the handle and the catheter lumen.

In another embodiment, the balloon catheter movement mechanism of the medical device may be configured for advancement and retraction of the balloon catheter through the handle and catheter lumen by user operation of the balloon catheter movement mechanism involving translation of the balloon catheter movement mechanism relative to the handle, by user operation of the balloon catheter movement mechanism involving longitudinal sliding of the balloon catheter movement mechanism along handle or by user operation of the balloon catheter movement mechanism involving rotation of at least a portion of the balloon catheter movement mechanism.

In a further embodiment, the guide wire movement mechanism of the medical device is configured for advancement and retraction of the guide wire through the handle and the catheter lumen by user operation of the guide wire movement mechanism involving translation of the guide wire movement mechanism relative to the handle or by user operation of the guide wire movement mechanism involving longitudinal sliding of the guide wire movement mechanism along the handle.

In another embodiment of the medical device, the guide catheter is configured for attachment, detachment and reattachment to the handle or the device further includes a guide tip configured for attachment, detachment and reattachment to the guide catheter.

In another embodiment of the medical device, a suction pathway is included for removal or material from the paranasal sinus or the sinus canal or an irrigation cartridge is included for irrigating the paranasal sinus or sinus canal.

In a further embodiment, the medical device includes a guide wire support disposed within the handle. The guide wire is at least partially disposed within the guide wire support and the guide wire support is configured to prevent buckling of the guide wire within the handle during advancement of the guide wire through the handle. The guide wire support may be generally cylindrical in shape and may include a slit-shaped opening configured such that, during advancement of the guide wire, the guide wire enters the guide wire support via the slit-shaped opening.

In another embodiment of the medical device, the guide wire locking and rotation mechanism includes a barrel with an axial opening and a collet axle at least partially disposed within the axial opening of the barrel.

In a further embodiment of the medical device, the guide wire movement mechanism includes at least one rail configured for sliding movement of the guide wire mechanism along a length of the handle during advancement and retraction of the guide wire.

In yet another embodiment of the medical device, the balloon catheter movement mechanism includes at least one rail configured for sliding movement of the balloon catheter mechanism along a length of the handle during advancement and retraction of the balloon catheter.

In another embodiment the guide wire movement mechanism and the balloon catheter movement mechanism are disposed on the handle in a configuration for single-handed operation of both the guide wire movement mechanism and the balloon catheter movement mechanism by a user. The guide wire movement mechanism and the balloon catheter movement mechanism may be disposed on the handle in an in-line configuration along the length of the handle or in a side-by-side configuration.

In another embodiment of the medical device, the sinus opening for treatment may be at least one of a Frontal sinus opening, Maxillary sinus opening, and Sphenoid sinus opening.

In yet another embodiment of the medical device, the guide wire locking and rotation mechanism is configured for thumb-operated rotation or single finger operated rotation of the guide wire.

In another aspect, a method is provided for treating a sinus opening. The method includes inserting a medical device for the treatment of a sinus opening partially into a patient's anatomy, positioning the medical device in the sinus opening, advancing a guide wire of the medical device into the patient's sinus via user operation of a guide wire movement mechanism of the medical device disposed on a handle of the medical device, rotating the guide wire within the patient's sinus via user operation of an integrated guide wire locking and rotation mechanism of the guide wire movement mechanism, repeating the guide wire advancing and rotating steps to position the guide wire in the sinus opening as appropriate for treatment, advancing a balloon catheter of the medical device along the guide wire via user operation of a balloon catheter movement mechanism of the medical device disposed on the handle of the medical device, and treating the sinus opening via inflation of the balloon catheter.

In one embodiment of the method, advancing the guide wire includes user operation of the guide wire movement mechanism involving translation of the guide wire movement mechanism relative to the handle or longitudinal sliding of the guide wire movement mechanism along the handle In another embodiment of the method, advancing the balloon catheter includes user operation of the balloon catheter movement mechanism involving translation of the balloon catheter movement mechanism relative to the handle, longitudinal sliding of the balloon catheter movement mechanism along handle, or rotation of at least a portion of the balloon catheter movement mechanism.

In a further embodiment, the method may further include deflating the balloon catheter, retracting the balloon catheter and the guide wire, and removing the medical device from the patient's anatomy.

In another embodiment, the method may include attaching, prior to the inserting step, a detachable guide tip to the medical device in an orientation appropriate for the sinus opening to be treated or attaching, prior to the inserting step, a detachable guide catheter to the medical device in an orientation appropriate for the sinus opening to be treated.

In a further embodiment of the method, the guide wire advancing step may include advancing the guide wire through a guide wire support disposed in the handle of the medical device and configured to prevent buckling of the guide wire in the handle.

In another embodiment of the method, the guide wire support is essentially cylindrical in shape and includes a slit-shaped opening through which the guide wire is directed by the guide wire movement mechanism.

In a further embodiment of the method, the patient's anatomy is a nostril and the sinus opening may be one of a Frontal sinus opening, Maxillary sinus opening, and Sphenoid sinus opening.

In another embodiment of the method, the guide wire movement mechanism and the balloon catheter movement mechanism are disposed on the handle in a configuration for single-handed user operation of both the guide wire movement mechanism and the balloon catheter movement mechanism by a user and may be in an in-line configuration along the length of the handle.

In other embodiments of the method, the guide wire locking and rotation mechanism is configured for thumb-operated or single finger operated rotation of the guide wire.

In a further embodiment, the method may include irrigating the sinus opening using the medical device and the irrigating may be accomplished using an irrigation cartridge installed in the medical device or an irrigation balloon catheter incorporated into the medical device.

In yet another embodiment, the method may include suctioning the sinus opening using the medical device.

BRIEF DESCRIPTION OF THE DRAWINGS

FIGS. 7A and 7B are simplified side and cross-sectional views, respectively, of the medical device of FIG. 6.

FIG. 12 is a simplified cross-sectional view of the guide wire movement mechanism and guide wire of FIG. 11 in a locked position.

FIG. 13 is a simplified cross-sectional view of the guide wire movement mechanism and guide wire of FIG. 11 in an unlocked position.

FIG. 14 is a simplified transparent view of the guide wire movement mechanism and guide wire of FIG. 11 in the absence of the barrel of the guide wire movement mechanism.

FIGS. 15A, 15B, and 15C are simplified perspective, top and side views, respectively, of a guide wire support as can be employed in medical devices according to the present invention with FIG. 15B also depicting a guide wire.

FIG. 16 is a simplified perspective view of the guide wire, balloon catheter, balloon catheter movement mechanism, guide wire movement mechanism and guide wire support of the medical device of FIG. 6 with the balloon working segment shown in an inflated state for clarity.

FIGS. 17A, 17B and 17C are a sequence of simplified perspective views of the guide wire, balloon catheter, balloon catheter movement mechanism, guide wire movement mechanism and guide wire support of FIG. 16 depicting the advancement of the guide wire by movement of the guide wire through a window opening of the guide wire support (FIGS. 17A and 17B) and through a slit of the guide wire support (FIG. 17C).

FIG. 19 is a simplified side view of the medical device of FIG. 6 depicting the guide wire movement mechanism in an advanced position and with arrows indicating how rotational movement of the barrel of the guide wire movement mechanism serves to rotate the guide wire.

FIG. 20 is a simplified side view of the medical device of FIG. 6 depicting the guide wire movement mechanism in a fully advanced position.

FIGS. 27A and 27B are views of the guide catheter locking mechanism of the device of FIG. 24 for 8 different rotational orientations according to the invention.

FIGS. 30A and 30B are top and side views of the balloon catheter of the device of FIG. 24 according to the invention and FIG. 30C shows further detail of the side view shown in FIG. 30B.

DETAILED DESCRIPTION OF INVENTION

Figure 1:
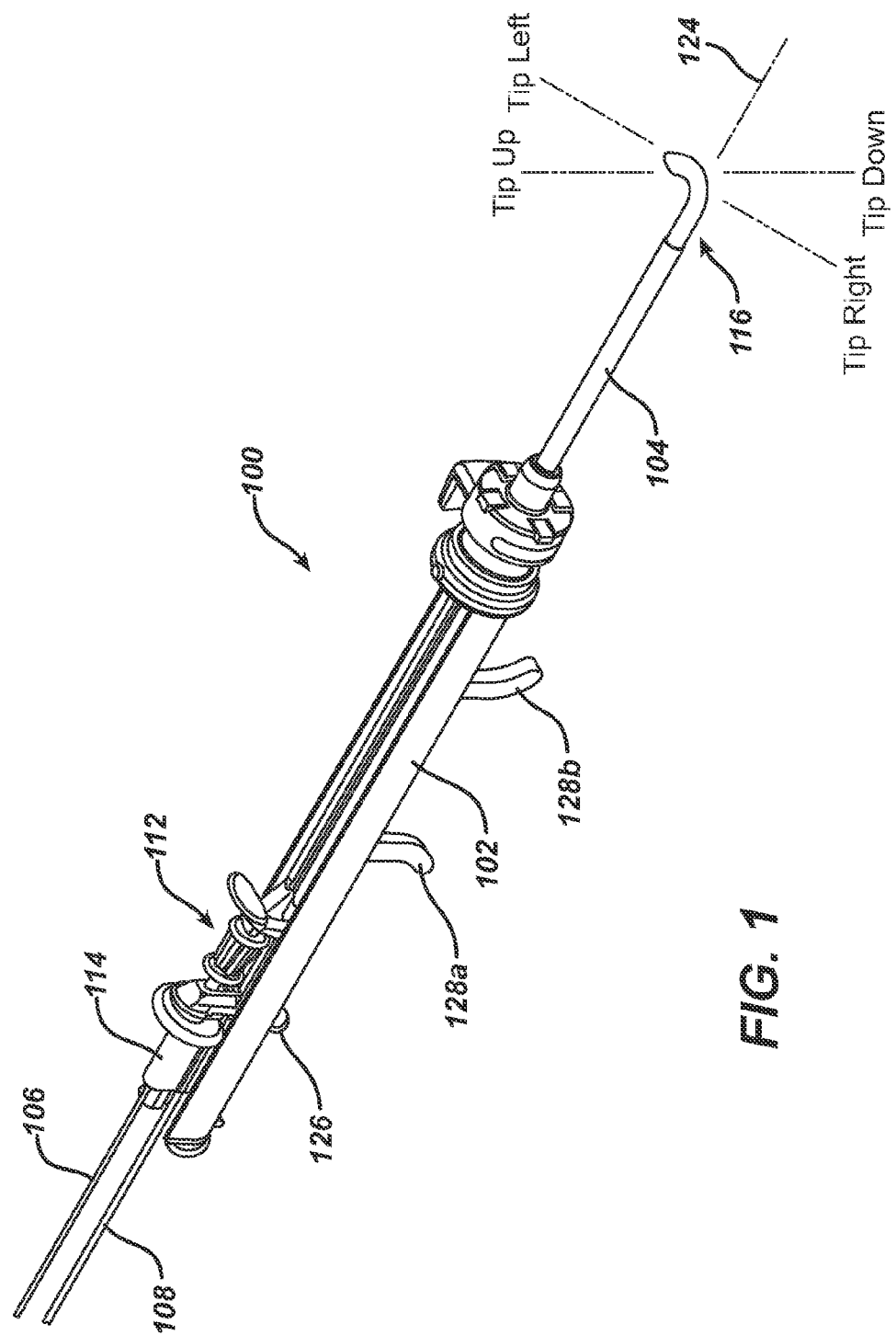
FIG. 1 is a simplified perspective view of a medical device for the treatment of a sinus opening according to an embodiment of the present invention.

The following detailed description should be read with reference to the drawings, in which like elements in different drawings are identically numbered. The drawings, which are not necessarily to scale, depict exemplary embodiments for the purpose of explanation only and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein.

In general, medical devices for the treatment (e.g., Balloon Sinuplasty™) of a sinus opening (for example, a Frontal, Maxillary, or Sphenoid sinus opening) according to embodiments of the present invention include a handle, a balloon catheter, a guide catheter, a guide wire, a guide wire movement mechanism and a balloon catheter movement mechanism. The handle has proximal and distal ends and a longitudinal axis along the length of the handle. The guide catheter is attached to the distal end of the handle and has a catheter lumen. Moreover, the handle and catheter lumen are configured for operatively accepting a guide wire and a balloon catheter. The guide wire movement mechanism and the balloon catheter movement mechanism are both operatively disposed on the handle. In addition, the guide wire movement mechanism is configured for advancement and retraction of a guide wire at least partially disposed in the handle and catheter lumen through the handle and catheter lumen by user operation of the guide wire movement mechanism. Moreover, the guide wire movement mechanism includes an integrated guide wire locking and rotation mechanism configured for rotation of the guide wire and for securely locking and unlocking the guide wire to the guide wire movement mechanism. Furthermore, the balloon catheter movement mechanism is configured for advancement and retraction of a balloon catheter at least partially disposed in the handle and catheter lumen through the handle and catheter lumen by user operation of the balloon catheter movement mechanism.

Medical devices according to embodiments of the present invention are beneficial in that the disposition of the guide wire movement mechanism and the balloon catheter movement mechanism on the handle of the medical device, combined in some embodiments with the sliding movement of the guide wire movement mechanism and the balloon catheter movement mechanism along the handle, provides a medical device that is particularly easy to use. For example, a physician can, if desired, operate the guide wire movement mechanism and the balloon catheter movement mechanism with a single hand. Moreover, since the guide wire movement mechanism is configured for guide wire rotation, locking and unlocking, in addition to guide wire advancement and retraction, ease of use (including single-handed use) is further increased. Moreover, the configuration of medical devices according to embodiments of the present invention enables a user to manipulate the guide catheter and guide wire simultaneously.

FIG. 1 is a simplified perspective view of a medical device 100 for the treatment of a sinus opening (for example, a Frontal, Maxillary or Sphenoid sinus opening) according to an embodiment of the present invention. FIG. 1 includes a marker depicting tip up, tip left, tip down and tip right orientations of a guide tip included in medical devices according to embodiments of the present invention.

Figure 2:
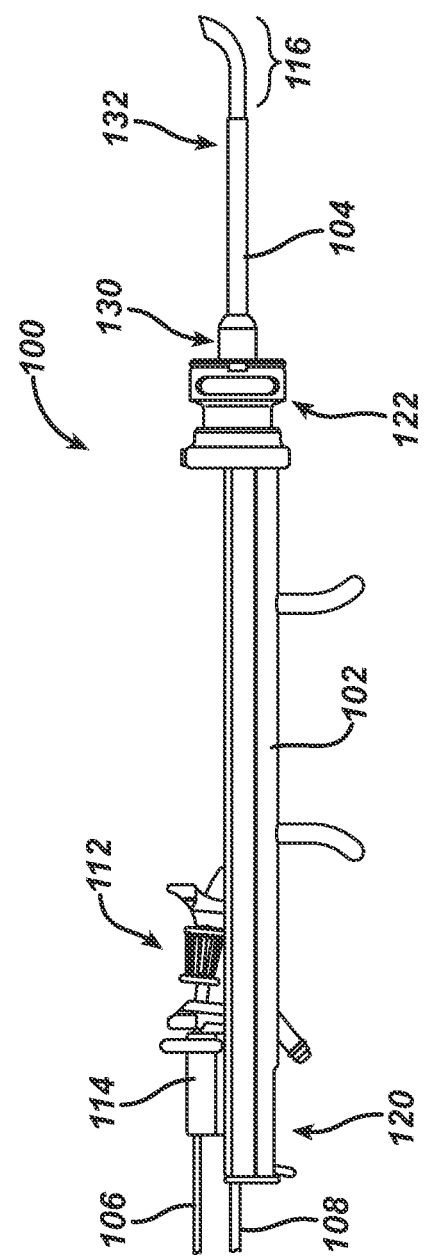
FIG. 2 is a simplified side view of the medical device of FIG. 1.
Figure 3:
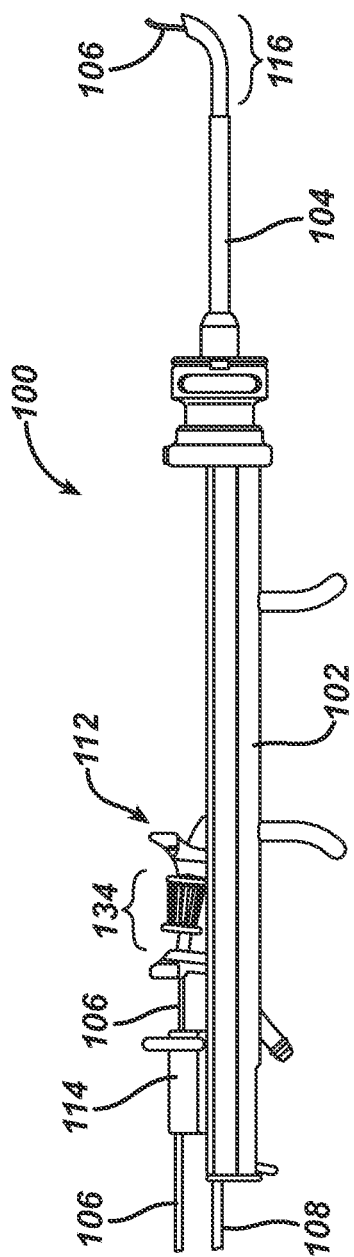
FIG. 3 is a simplified side view of the medical device of FIG. 1 with a guide wire of the medical device advanced.
Figure 4:
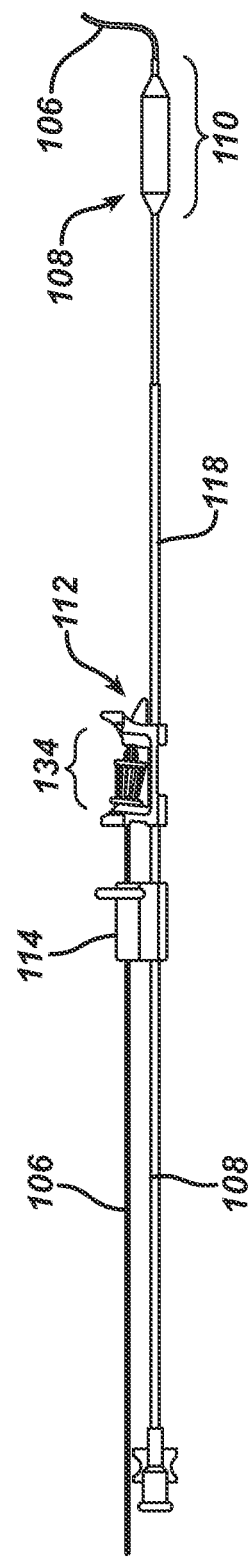
FIG. 4 is a simplified side view of the guide wire, balloon catheter, balloon catheter movement mechanism, guide wire movement mechanism and guide wire support of the medical device of FIG. 1 with a balloon working segment of the balloon catheter shown in an inflated state for clarity.
Figure 5:
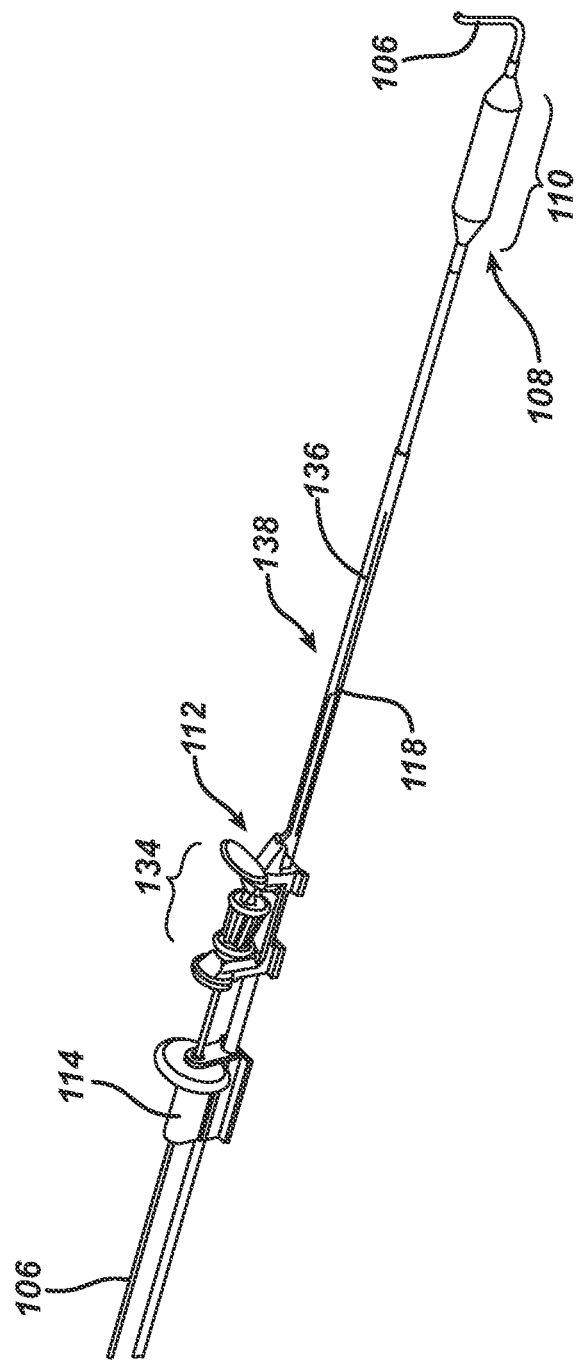
FIG. 5 is a simplified perspective view of the guide wire, balloon catheter, balloon catheter movement mechanism, guide wire movement mechanism and guide wire support of the medical device of FIG. 4.

FIG. 2 is a simplified side view of medical device 100. FIG. 3 is a simplified side view of medical device 100 with a guide wire and guide wire movement mechanism of the medical device in an advanced position. FIG. 4 is a simplified side view of the guide wire, balloon catheter, balloon catheter movement mechanism, guide wire movement mechanism and guide wire support of medical device 100, with a balloon working segment of the balloon catheter shown in an inflated state for clarity. FIG. 5 is a simplified perspective view of the guide wire, balloon catheter, balloon catheter movement mechanism, guide wire movement mechanism and guide wire support of FIG. 4.

Referring to FIGS. 1-5, medical device 100 for the treatment of a sinus opening includes a handle 102, a guide catheter 104, a guide wire 106, a balloon catheter 108 with a working balloon segment 110 (see FIGS. 4 and 5 in particular), a guide wire movement mechanism 112, a balloon catheter movement mechanism 114, a detachable guide tip 116 (shown with a curved (angled) tip in a "tip up" orientation), and a guide wire support 118 (see FIGS. 4 and 5). Alternative embodiments where the guide catheter is integral with the guide tip will be discussed below.

Handle 102 includes a proximal end 120, a distal end 122 and has a longitudinal axis 124 (the extension of which is represented by a dashed line in FIG. 1) along the length of handle 102. Handle 102 includes suction access barb 126 and finger anchoring pegs 128a and 128b (see FIG. 2). Handle 102 is sized and shaped such that medical device 100 can be manipulated and operated by a user (such as a physician) in a convenient and efficient single-handed manner if so desired. Handle 102 can be formed of any suitable material including, for example, polycarbonate and ABS (acetonitrile butadiene styrene) and can be manufactured using any suitable technique including, for example, injection molding of two clam shell handle halves.

Guide catheter 104 is attached to distal end 122 of handle 102 and has a catheter lumen (i.e., inner passage, not visible in the perspectives of FIGS. 1-3) therein. Guide catheter 104 has a proximal end 130 and a distal end 132 (see FIG. 2). Guide catheter 104 can be formed of any suitable materials including, for example, stainless steel, polymeric materials and combinations thereof. A typical but non-limiting inner diameter for a guide catheter is between about 0.070 and 0.150 inches.

In the embodiment of FIGS. 1-5, detachable guide tip 116 is configured for removable attachment to, and detachment from, distal end 132 of guide catheter 104. However, detachable tips employed in medical devices according to the present invention can be attached and detached from the medical device at any suitable location on the medical device. For example, the detachable guide tip can be attached anywhere along the guide catheter or at the distal end of the handle. Detachable guide tip 116 can be formed of any suitable material including, for example, stainless steel, polymeric materials and combinations thereof.

Guide wire 106 is disposed at least partially in handle 102, guide wire support 118 and the catheter lumen of guide catheter 104. Guide wire 106 can be any suitable guide wire known to one skilled in the art including, for example, an illuminated guide wire configured to provide a user with confirmation of sinus access. Balloon catheter 108 is disposed at least partially in handle 102 and the catheter lumen of guide catheter 104 and can be any suitable balloon catheter known to one skilled in the art as well as the balloon catheters described herein.

Guide wire movement mechanism 112 is operatively disposed on handle 102 and configured for advancement and retraction of guide wire 106 through handle 102, guide wire support 118 and the catheter lumen of guide catheter 104 by longitudinal sliding of guide wire movement mechanism 112 along the length of handle. A comparison of FIGS. 2 and 3 serves to convey how movement of guide wire movement mechanism 112 along handle 102 serves to advance guide wire 106 such that guide wire 106 extends from detachable guide tip 116.

Guide wire movement mechanism 112 includes an integrated guide wire locking and rotation mechanism 134 configured for rotation of guide wire 106 and for securely locking and unlocking guide wire 106 to guide wire movement mechanism 112. Further details of such an integrated guide wire locking and rotation mechanism are described below with respect to FIGS. 11 through 14.

Once apprised of the present disclosure, one skilled in the art will recognize that guide wire movement mechanisms employed in medical devices (and methods) according to the present invention are not limited to those that are user operated via sliding along the length of the handle. Rather, user operation of the guide wire movement mechanism can be any suitable operation that results in operable movement of the guide wire by, for example, translation (i.e., movement that changes the position of an object) of the guide wire movement mechanism relative the handle or rotation of a guide wire movement mechanism component. In this regard, the configuration of the guide wire movement mechanism would support such user operation via a suitable rack and pinion mechanism, gears, and/or electromechanical means.

Balloon catheter movement mechanism 114 is operatively disposed on handle 102 and configured for advancement and retraction of balloon catheter 108 through handle 102 and the guide catheter lumen by longitudinal sliding of the balloon catheter movement mechanism along the handle. However, once apprised of the present disclosure, one skilled in the art will recognize that balloon catheter movement mechanisms employed in medical devices (and methods) according to the present invention are not limited to those that are user operated via longitudinal sliding along the length of the handle. Rather, user operation of the balloon catheter movement mechanism can be any suitable operation that results in operable movement of the balloon catheter by, for example, translation of the balloon catheter movement mechanism relative to the handle or rotation of a balloon catheter movement mechanism component. In this regard, the configuration of the balloon catheter mechanism would support such user operation via suitable rack and pinion mechanism, gear-based mechanisms, and/or electromechanical means.

Guide wire support 118 of medical device 100 is operatively disposed within handle 102 and provides additional column strength to guide wire 106 and prevents guide wire 106 from buckling within handle 102 during advancement. Guide wire support 118 includes a slit-shaped opening 136 (see FIG. 5) into which guide wire 106 is fed by guide wire movement mechanism 112. Further details of guide wire supports that can be employed in embodiments of the present invention are described below in regard to, for example, FIGS. 15A-15C, 16 and 17A-17C.

Figure 6:
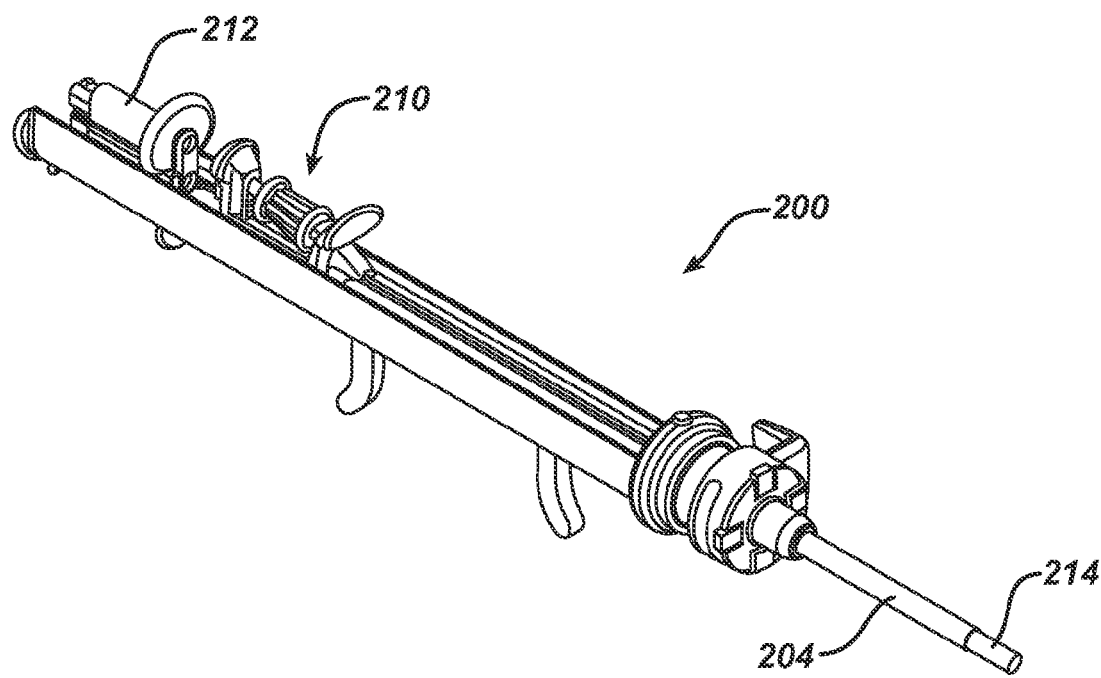
FIG. 6 is a simplified perspective view of a medical device for the treatment of a sinus opening (absent a guide wire, guide tip and balloon catheter) according to another embodiment of the present invention.
Figure 7A:
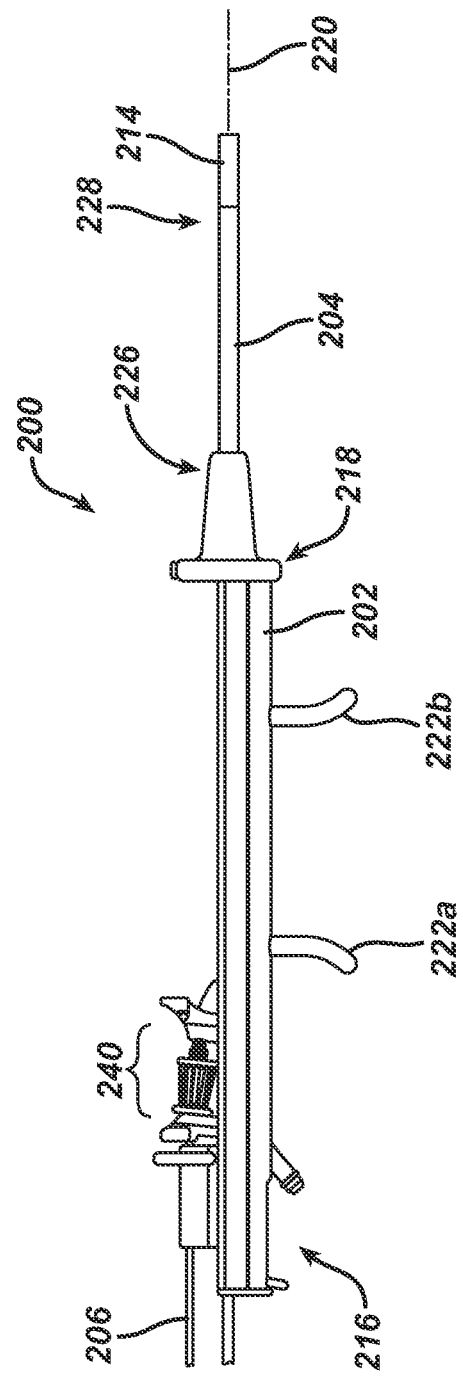
Figure 8:
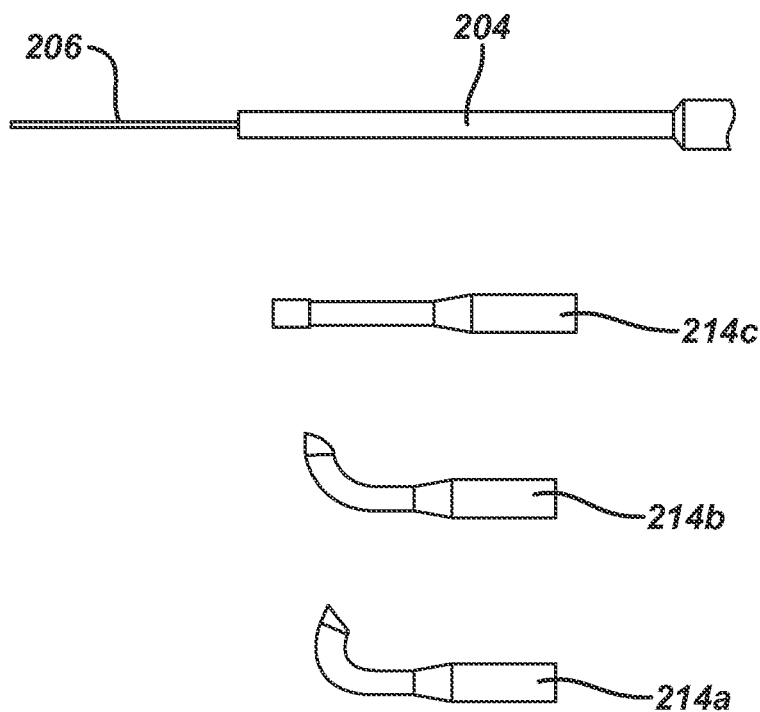
FIG. 8 is a simplified depiction of a portion of a guide catheter and three detachable guide tips as can be employed in a medical device according to embodiments of the present invention.

FIG. 6 is a simplified perspective view of a medical device 200 for the treatment of a sinus opening according to an embodiment of the present invention. FIGS. 7A and 7B are simplified side and cross-sectional views, respectively, of medical device 200. FIG. 8 is a simplified depiction of a portion of a guide catheter and three guide tips (also referred to as detachable guide tips) as can be employed in a medical device according to embodiments of the present invention.

Figure 9:
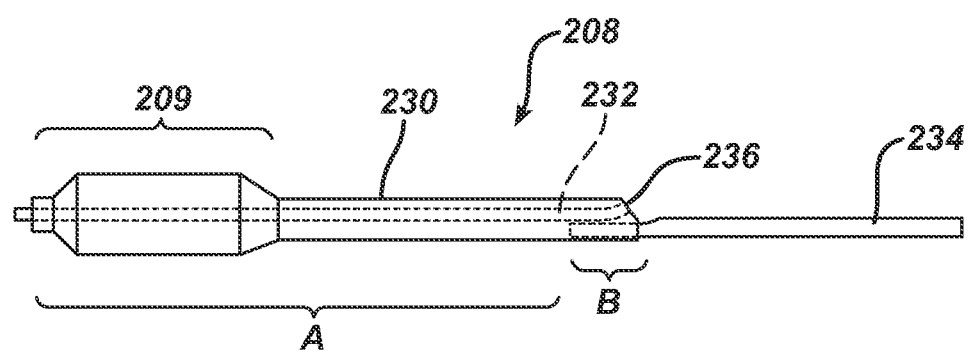
FIG. 9 is a simplified cross-sectional depiction of a balloon catheter as can be employed in medical devices according to the present invention.
Figure 10:
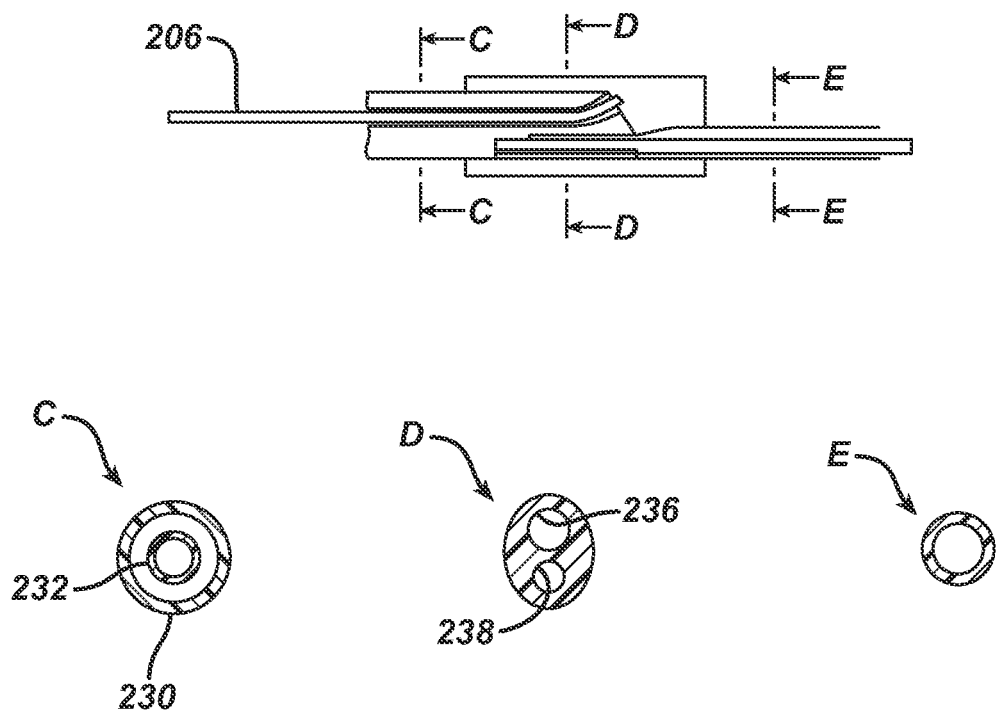
FIG. 10 is a combined longitudinal and triple cross-sectional depiction of a portion of the balloon catheter of FIG. 9 along with a portion of a guide wire.
Figure 11:
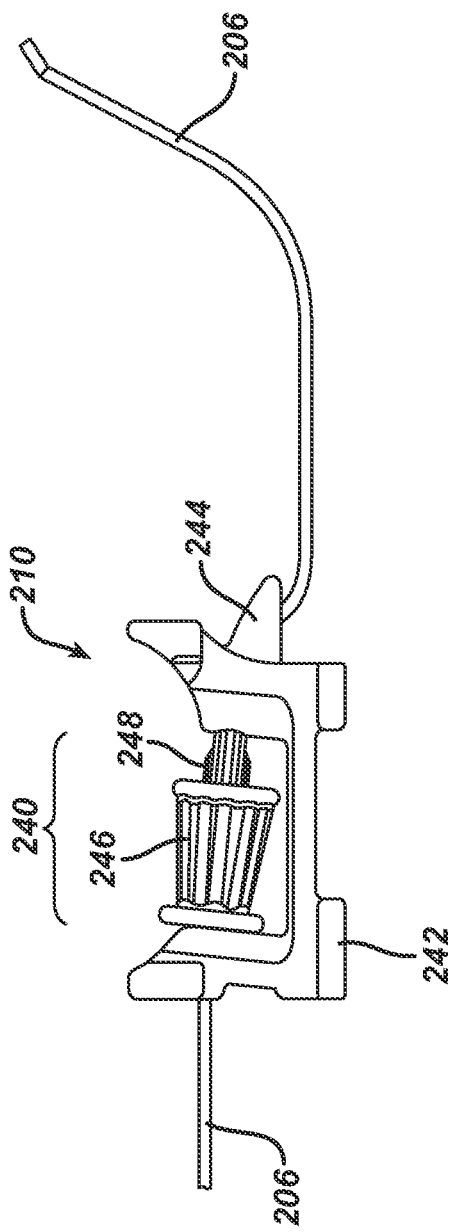
FIG. 11 is a simplified side view of a guide wire movement mechanism and guide wire of the medical device of FIG. 6.

FIG. 9 is a simplified cross-sectional depiction of a balloon catheter as can be employed in medical devices according to the present invention. FIG. 10 is a combined longitudinal and triple cross-sectional depiction of a portion of the balloon catheter of FIG. 9 along with a portion of a guide wire and a portion of a balloon inflation tube.

FIGS. 11 through 14 are various simplified depictions of a guide wire movement mechanism and guide wire of medical device 200. FIGS. 15A, 15B and 15C are various simplified views of a guide wire support employed in medical device 200, with FIG. 15B also depicting a portion of a guide wire. FIG. 16 is a simplified perspective view of the guide wire, balloon catheter, balloon catheter movement mechanism, guide wire movement mechanism and guide wire support of medical device 200, with the balloon working segment shown in an inflated state for clarity. FIGS. 17A, 17B and 17C are a sequence of simplified perspective views of the of the guide wire, balloon catheter, balloon catheter movement mechanism, guide wire movement mechanism and guide wire support of FIG. 16 that depict the advancement of the guide wire including movement of the guide wire through a window opening of the guide wire support (FIGS. 17A and 17B) and through a slit-shaped opening of the guide wire support (FIG. 17C).

Referring to FIGS. 6 through 17C, medical device 200 for the treatment of a sinus opening includes a handle 202, a guide catheter 204, a guide wire 206 (not included in FIG. 6 but see, for example, FIGS. 7 and 8), a balloon catheter 208 with balloon working segment 209 (see FIGS. 9 and 16 in particular), a guide wire movement mechanism 210, a balloon catheter movement mechanism 212, and a detachable guide tip 214. It should be noted that medical device 200 differs from medical device 100 in that, for example, detachable guide tip 214 of medical device 200 is straight (i.e., has an angle of zero (0) degrees) while detachable guide tip 114 of medical device 100 has an angle. The benefits of curved and straight detachable tips in efficiently treating various sinus openings are discussed below.

Handle 202 includes a proximal end 216, a distal end 218 and has a longitudinal axis 220 along the length of handle 202 indicated by the dashed line in FIG. 7A. Handle 202 includes finger anchoring pegs 222a and 222b and is sized and shaped such that medical device 200 can be manipulated and operated, if desired, by a user (such as a physician) in a single-handed manner.

Guide catheter 204 is attached to distal end 218 of handle 202 and has a catheter lumen (i.e., inner passage) 224 therein (see FIG. 7B). Guide catheter 204 has a proximal end 226 and a distal end 228.

Detachable guide tip 214 of medical device 200 is configured for removable attachment to, and detachment from, distal end 228 of guide catheter 204. FIG. 8 depicts three exemplary, but non-limiting, guide tips 214a, 214b and 214c, a portion of guide catheter 204 and guide wire 206. Attachment and detachment of guide tips in medical devices according to embodiments of the present invention can be accomplished using any suitable means including a clip, push button, and bayonet style mechanism.

Guide tips 214a, 214b and 214c of FIG. 8 each are configured to include angles (from 0 degrees to 110 degrees) that make them particularly suitable for treatment of various sinus openings. Moreover, the detachable configuration of the guide catheter and the guide tips is such that the guide tips can be attached to the medical device (for example attached to the guide catheter) in a predetermined orientation with respect to the remainder of the medical device or attached in one orientation and then rotated into another orientation. For example, for treatment of a Frontal sinus opening, a guide tip with an angle of 70 to 90 degrees can be employed with the guide tip attached or rotated into in a "tip right" configuration for a right-handed user operating the medical device with the user's right-hand thumb. This orientation ensures the controls will be most accessible to the user's dominant digit when the user is operating the guide wire movement mechanism and/or balloon catheter movement mechanism of the medical device.

For the treatment of the Maxillary sinuses, a preferred orientation of the guide tip depends on the side (e.g., Right or Left Maxillary) of the sinus opening being treated in addition to the user's dominant hand and actuating digit. For treatment of a Right Maxillary sinus opening, a guide tip with an angle of 90 to 110 degrees can be employed with the guide tip in a "tip up" orientation for a right-handed user operating the medical device with the user's thumb. For treatment of a Left Maxillary sinus opening, a guide tip with an angle of 90 to 110 degrees can be employed with the guide tip in a "tip down" orientation for a right-handed user operating the medical device with the user's thumb. For treatment of a Right Sphenoid sinus opening, a guide tip with an angle of 0 to 30 degrees can be employed with the guide tip in a "tip up" orientation (if the guide tip is angled) for a right-handed user operating the medical device with the user's thumb. For treatment of a Left Sphenoid sinus opening, a guide tip with an angle of 0 to 30 degrees can be employed with the guide tip in a "tip down" orientation for a right-handed user operating the medical device with the user's thumb. Table 1 summarizes a preferred guide tip angle, and the guide tip orientation for a right-handed user operating (actuating) the medical device controls (i.e., the guide wire movement mechanism and the balloon catheter movement mechanism). The orientations are as marked in FIG. 1.

TABLE 1

Tip Orientation Based on User and Sinus Type

| | | Preferred Guide Tip Angle (in degrees) | Right Handed User Actuating Controls with Thumb | Right Handed User Actuating Controls with Forefinger |
|---|---|---|---|---|
| Sinus Type | Frontal | 70-90 | Tip Right | Tip Up |
| | Right Maxillary | 90-110 | Tip Up | Tip Left |
| | Left Maxillary | 90-110 | Tip Down | Tip Right |
| | Right Sphenoid (assuming an angled tip) | 0-30 | Tip Up | Tip Left |
| | Left Sphenoid (assuming an angled tip) | 0-30 | Tip Down | Tip Right |

Guide wire 206 is disposed at least partially in handle 202 and catheter lumen 224. Guide wire 106 can be any suitable guide wire known to one skilled in the art including, for example, an illuminated guide wire.

Balloon catheter 208 is also disposed at least partially in handle 202 and catheter lumen 224. Referring to FIGS. 9 and 10, balloon catheter 208 includes an outer shaft 230, inner shaft 232 and proximal shaft 234. Balloon catheter 208 also includes a guide wire access opening 236.

Balloon catheter 208 includes a section (labeled A in FIG. 9) with a co-axial lumen design and a section (labeled B in FIG. 9) wherein the outer shaft, inner shaft and proximal shaft are joined together in a manner that provides for a transition between a co-axial configuration, a dual lumen configuration and a single lumen proximal shaft. FIG. 10 (an exemplary, but non-limiting, depiction of a manner in which guide wire 206 and balloon catheter 208 can interact within handle 202 of medical device 200) includes three simplified cross-sectional depictions. Cross-sectional illustration "C" depicts a coaxial arrangement of the outer shaft and inner shaft taken along line C-C of FIG. 10. Cross-sectional illustration "D" depicts a dual lumen (i.e., guide wire access opening 236 and balloon catheter inflation lumen 238) configuration taken along line D-D of FIG. 10. Cross-sectional illustration "E" (taken along line E-E of FIG. 10) depicts a single lumen (i.e., the balloon catheter inflation lumen) configuration.

The co-axial design of segment A provides a beneficially small profile to fit into the guide shaft of medical device 200. Moreover, since there is only a single dual lumen segment (i.e., segment B) in addition to the co-axial segment, medical devices incorporating the configuration of FIGS. 9 and 10 require relatively low complexity manufacturing. However, once apprised of the present disclosure, one skilled in the art will recognize that balloon catheters employed in medical devices and methods according to embodiments of the present invention can have any suitable configuration and are not limited to the configuration of FIGS. 9 and 10. For example, a balloon catheter employed in medical devices and methods according to embodiments of the present invention can include a dual lumen segment that extends to the distal end of the balloon catheter in place of the co-axial segment depicted in FIGS. 9 and 10. In such a configuration, the guide wire access lumen would have an opening at the distal end of the balloon catheter through which the guide wire would be advanced and the balloon catheter inflation lumen would have an opening at the balloon working segment for inflation of the balloon working segment.

Moreover, construction of the balloon catheter shafts can be such that deleterious effects of forces (frictional or otherwise) between the catheter shaft and the guide wire during operation of the medical device are minimized. For example, a lubricious liner on the catheter shaft can be employed to minimize frictional forces between the guide wire and the balloon catheter shaft. In addition, the balloon catheter shaft can be of a braided construction to prevent collapse of the balloon catheter inner shaft onto the guide wire. Such a collapse can be of particular concern when the balloon catheter travels through the curve of a curved guide tip.

Balloon catheter 208 can be formed of any suitable material known to one skilled in the art including, for example, Nylon, Pebax or PET. The balloon catheter may be any size catheter including but not limited to 3.5 mm to 7 mm in diameter (when inflated) and 12 mm to 24 mm in working length (for example 3.5 mm×12 mm, 5 mm×16 mm, 5 mm×24 mm, 6 mm×16 mm, 6 mm×20 mm, 6 mm×24 mm, 7 mm×16 mm and 7 mm×24 mm. Moreover, balloon catheter 208, guide catheter 204 and handle 202 can be configured such that balloon catheter 208 is removable from guide catheter 204 and handle 202.

Guide wire movement mechanism 210 is operatively disposed on handle 202 (see, for example, FIGS. 6, 7A and 7B) and configured for advancement and retraction of guide wire 206 through handle 202 and catheter lumen 224 by user operation of guide wire movement mechanism 210. In medical device 200, such user operation involves longitudinal sliding of guide wire movement mechanism 210 along handle 202.

Guide wire movement mechanism 210 includes an integrated guide wire locking and rotation mechanism 240 configured for rotation of guide wire 206 and for securely locking and unlocking the guide wire to the guide wire movement mechanism, a rail 242, and a nosepiece 244. Rail 242 is configured for slidably attaching guide wire movement mechanism 210 to handle 202. Nosepiece 244 is configured to direct guide wire 206 into handle 202 and guide wire access opening 236 of balloon catheter 208 and, in the embodiment of medical device 200 into guide wire support 260 of medical device 200 as described further below with respect to FIGS. 11-17C.

Integrated guide wire locking and rotation mechanism 240 includes a barrel 246 and a collet axle 248 (see FIGS. 11-14 in particular). The locking/unlocking capability of integrated guide wire locking and rotation mechanism 240 enables a user to adjust the length of the guide wire extending (distally) beyond the guide wire movement mechanism 210.

Collet axle 248 is configured to function both as a collet and as an axle and has a longitudinal opening through which the guide wire 206 passes (see FIG. 13 in particular). In the embodiment of FIGS. 11 through 14, collet axle 248 is essentially cylindrical in overall shape, and when locked onto the guide wire 206 (see FIG. 12 where the depicted overlap of the barrel and the collet axle serves to illustrate that the barrel is compressing the collet axle onto the guide wire), rotates and translates with the guide wire. Collet axle 248 rotates within bearing surfaces 250 of the guide wire movement mechanism 210 (see FIG. 13). The collet axle has a plurality of alternating protrusions 252 and slots 254 (see FIG. 14) configured to lock (close) onto the guide wire, thereby linking rotation of the guide wire with rotation of the collet axle. Collet axle 248 exerts a strong clamping force on the guide wire when the collet axle is tightened via longitudinal movement of barrel 246 (as is evident from a comparison of FIG. 12 where the collet axle is locked into the guide wire and FIG. 13 where the collet axle is unlocked from the guide wire).

Barrel 246 has an essentially cylindrical cross-section and an opening therethrough, in which collet axle 248 is disposed. The contour of the barrel's opening is designed to receive the collet axle and has at least one focal point configured to collapse the collet axle onto the guide wire (see FIG. 12 in particular). The exterior of barrel 246 has grip features shown in the embodiment of FIGS. 11-13 as a macroscopic surface feature (i.e., ridges). However, such grip features could alternatively be microscopic in nature or based on frictional material properties such as a rubberized surface. Such grip features provide traction for the user to rotate or translate the barrel via operation with, for example, the user's thumb or finger which rotates the wire by rotation of the axle in which the wire is locked. The distal and proximal ends of the barrel have a raised ring feature 256, which provides traction for the user to translate the guide wire movement mechanism when the collet axle is in a locked position or provide a gripping feature to move the barrel relative to the remainder of the guide wire movement mechanism to lock and unlock the axle.

Once apprised of the present disclosure, one skilled in the art will recognize that guide wire locking and rotation mechanisms employed in medical devices according to the present invention can take any suitable form in addition to the barrel and collet axle configurations shown in, for example, FIGS. 11 through 14. For example, the barrel could be shaped essentially as a sphere, cylinder or other suitable shape.

Balloon catheter movement mechanism 212 is operatively disposed on handle 202 and configured for advancement and retraction of balloon catheter 208 through handle 202 and the guide catheter lumen by longitudinal sliding of the balloon catheter movement mechanism along the handle.

Referring now to FIGS. 15A through 17C in particular, medical device 200 includes an optional guide wire support 260 operatively disposed within handle 202 of medical device 200. Guide wire support 260 provides additional column strength to guide wire 206 and is configured to prevent guide wire 206 from buckling within handle 202.

Guide wire support 260 is configured as a thin walled tube having four sections, namely a proximal attachment section 262, a window section 264, a slit section 266, and a distal attachment section 268. Moreover, guide wire support 200 has a slit-shaped opening 270 in slit section 266 and a surface window opening 272 in window section 264 (see FIG. 15C). Guide wire support 260 can be formed of any suitable materials including, for example, polymeric materials, stainless steel materials, titanium alloys and combinations thereof.

It is noted that inclusion of a guide wire support in medical devices according to embodiments of the present invention is optional. For example, the guide wire support can be eliminated if other means for preventing or minimizing guide wire buckling (e.g., a geared tracking system for advancing the guide wire) are provided or guide wire buckling is not otherwise encountered during normal use of the medical device.

The sequence depicted in FIGS. 17A, 17B and 17C depict guide wire movement mechanism 210 being advanced by a user. In FIGS. 17A and 17B, guide wire 206 exits guide wire movement mechanism 210 and enters surface window opening 272. In FIG. 17C, the user has advanced guide wire movement mechanism 210 further such that guide wire 206 enters slit-shaped opening 270. Slit-shape opening 270 is configured such that it opens as guide wire 206 is advanced. The slit-shape opening 270 extends distally of the surface window opening 272. The slit-shape opening 270 prevents buckling of the guide wire 206 and the surface window opening 272 provides a region of lower friction for ease of movement of the guide wire 206 within the nasal anatomy.

Once apprised of the present disclosure, one skilled in the art will recognize that guide wire supports employed in medical devices according to embodiments of the present invention can have any suitable configuration and are not limited to the configuration depicted in FIGS. 15A through 17C. For example, a suitable guide wire support can be a cylinder with a lumen and a surface window opening (with the lumen and surface window opening configured for accepting a guide wire) and a coil or braid (e.g., a metallic or polymeric coil) wrapped around a portion of the cylinder including at least a portion of the surface window opening or a spiral shaped surface window opening on a rotating coil or tube. In such a guide wire support, the coil or braid is configured to prevent buckling of the guide wire through the surface window opening during advancement of the guide wire through the handle. Alternatively, the guide wire support can include a cylinder with a lumen and a surface window opening (the lumen and surface window opening configured for accepting a guide wire) and a telescoping encasement around a portion of the cylinder including at least a portion of the surface window opening. In this alternative, the telescoping encasement is configured to prevent buckling of the guide wire through the surface window opening during advancement of the guide wire through the handle.

Figure 18:
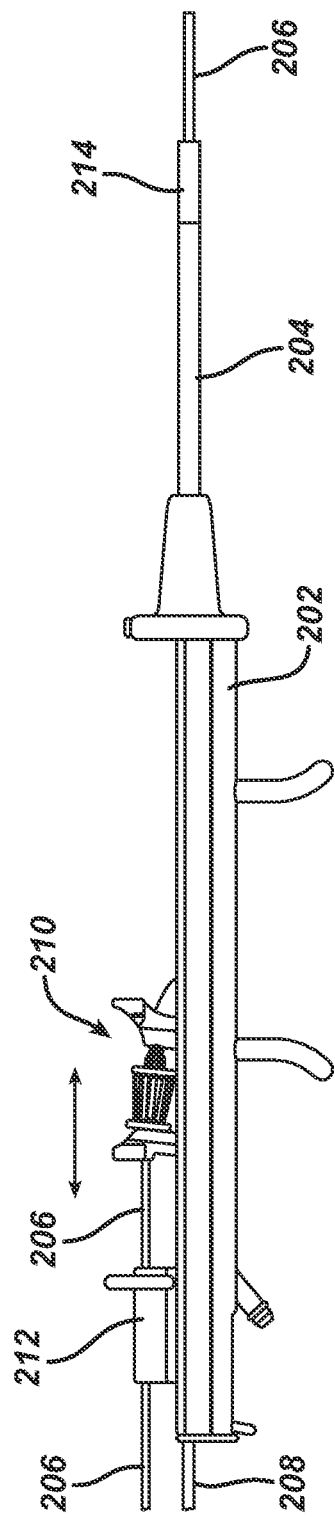
FIG. 18 is a simplified side view of the medical device of FIG. 6 depicting the guide wire movement mechanism in an advanced position.

Operation of medical device 200, including operation of guide wire movement mechanism 210 and balloon catheter movement mechanism 212 are further described below with respect to FIGS. 18 through 22. FIG. 18 is a simplified side view of the medical device 200 depicting guide wire movement mechanism 210 in an advanced position. The arrow of FIG. 18 indicates the directions in which guide wire movement mechanism 210 can move. In the advanced position of FIG. 18, guide wire movement mechanism 210 has slid, for example, approximately 2.0 to 4.0 cm from the position depicted in FIG. 7.

FIG. 19 is a simplified side view of medical device 200 depicting guide wire movement mechanism 210 in an advanced position and with arrows indicating the manner in which rotational movement of barrel 246 and collet axle 248 of guide wire movement mechanism 210 serves to rotate guide wire 206.

FIG. 20 is a simplified side view of the medical device 200 depicting guide wire movement mechanism 210 in a fully advanced position that is, for example, approximately 6.0-8.0 cm from the position of FIG. 7. Since guide wire movement mechanism 210 is further advanced in FIG. 20 than in FIG. 19, the length of guide wire 206 extending from detachable guide tip 214 is longer in FIG. 20 than in FIG. 19.

Figure 21:
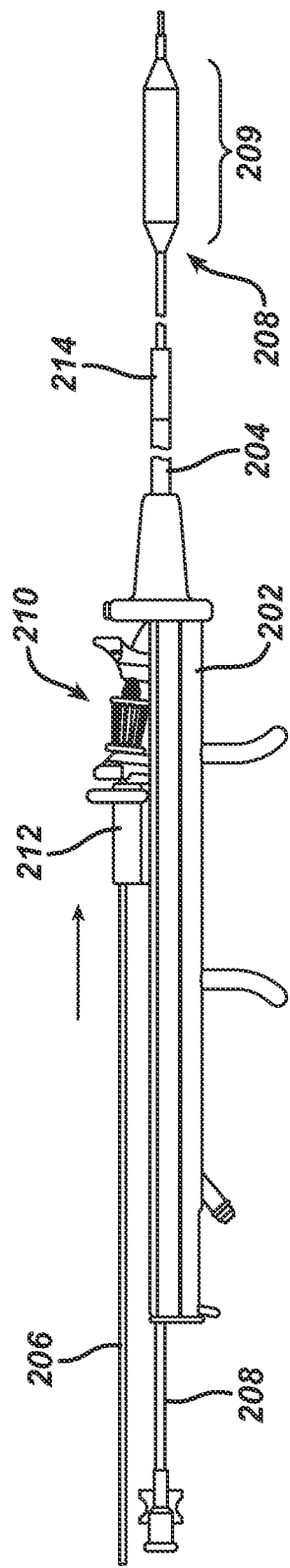
FIG. 21 is a simplified side view of the medical device of FIG. 6 depicting the balloon movement mechanism in a fully advanced position.

FIG. 21 is a simplified side view of the medical device 200 depicting balloon catheter movement mechanism 212 in a fully advanced position. The arrow of FIG. 21 depicts the sliding movement direction that balloon catheter movement mechanism 212 took to arrive at the fully advanced position. FIG. 21 depicts balloon catheter 208 in an inflated state as can be employed to treat a sinus opening.

Figure 22:
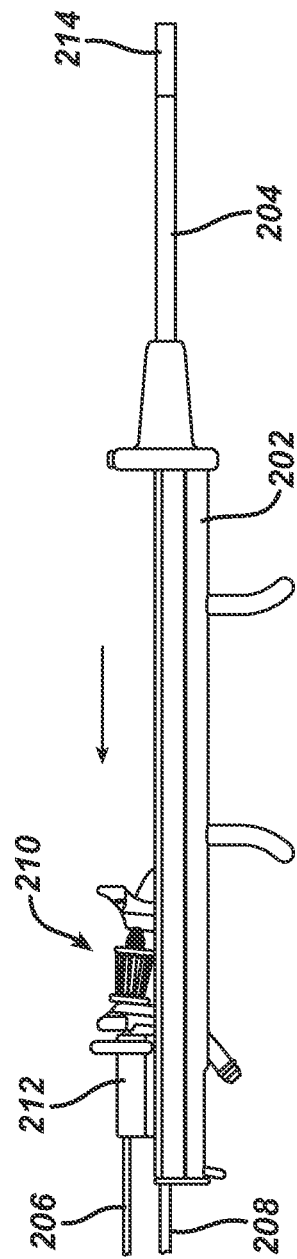
FIG. 22 is a simplified side view of the medical device of FIG. 6 depicting the balloon movement mechanism and the guide wire movement mechanism in a retracted position.

FIG. 22 is a simplified side view of medical device 200 depicting balloon catheter movement mechanism 212 and guide wire movement mechanism 210 in a retracted position with the arrow indicating their retraction direction.

In general, methods for treating a sinus opening include inserting a medical device for the treatment of a sinus opening partially into a patient's anatomy and advancing a guide wire of the medical device into the patient's sinus via user operation of a guide wire movement mechanism of the medical device that is disposed a handle of the medical device. The method also includes rotating the guide wire within the patient's sinus via user operation of a rotating component of the guide wire movement mechanism and repeating the guide wire advancing and rotating steps to position the guide wire in the sinus opening as appropriate for treatment. The method further includes advancing a balloon catheter of the medical device along the guide wire via user operation of a balloon catheter movement mechanism of the medical device that is disposed on the handle of the medical device; and treating the sinus opening via inflation of the balloon catheter.

Methods according to embodiments of the present invention are beneficial in that they employ a medical device that is relatively easy to set-up and the methods themselves are easy to perform. For example, the set-up can involve the attachment of an appropriate guide tip selected by a user from among a plurality of guide tips of various sizes and angles supplied with the medical device (see, for example, FIG. 8). The methods are easy to perform since, for example, the medical device can, if desired, be operated with one hand since both the guide wire movement mechanism and the balloon catheter movement mechanism are disposed on the handle of the medical device. Since the methods are easy to perform, they can be performed in both a hospital operating room and a medical office setting. Also, in various embodiments, the guide wire rotation and locking mechanism of the medical device employed in the methods can be thumb operated or operated by a single finger such as a forefinger. Moreover, should a user desire to treat more than one sinus opening, the amount of preparation between sinus is reduced by the use of a detachable guide tip.

Figure 23:
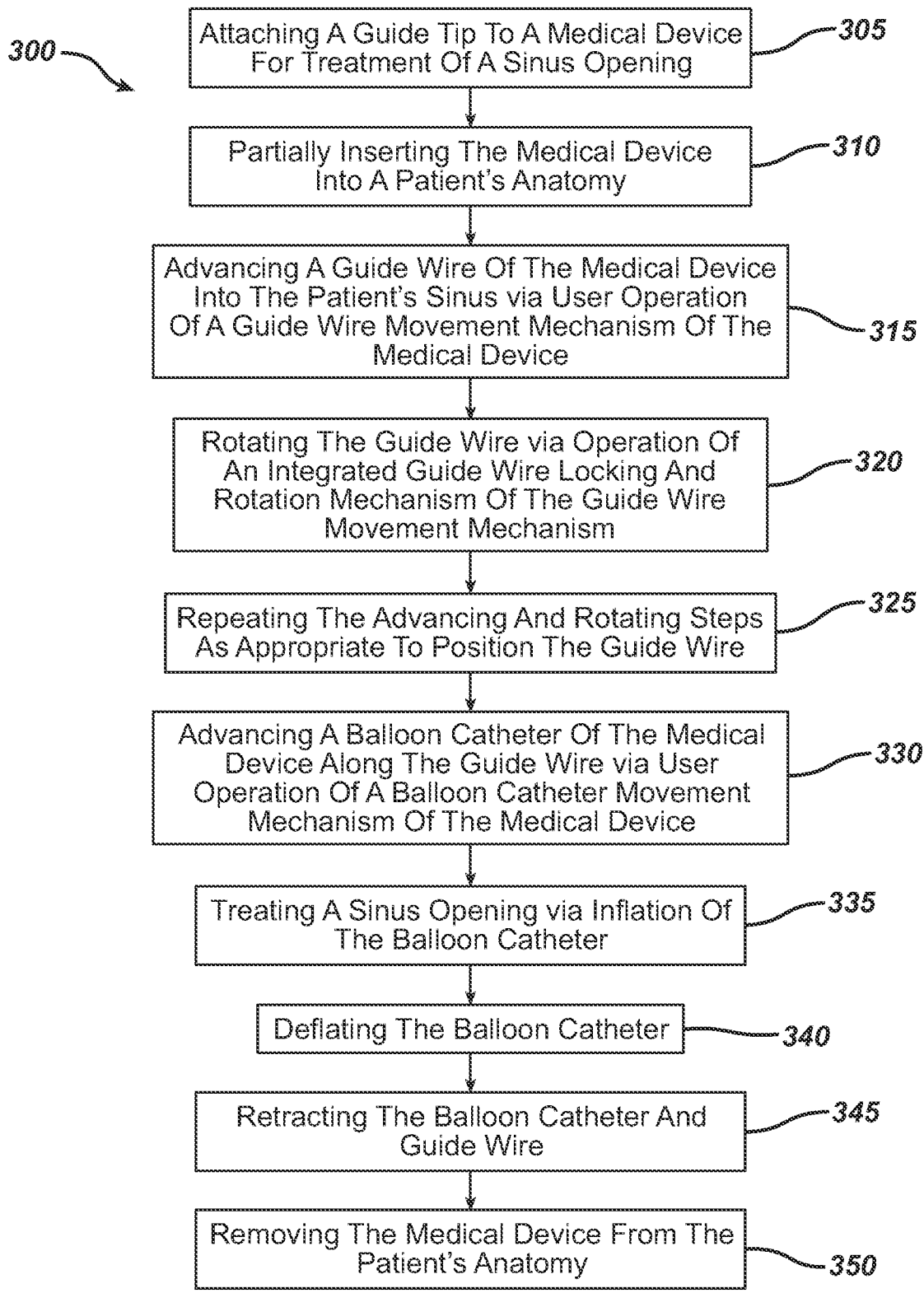
FIG. 23 is a flow diagram depicting stages in a method for treating a sinus opening according to an embodiment of the present invention.
Figure 24:
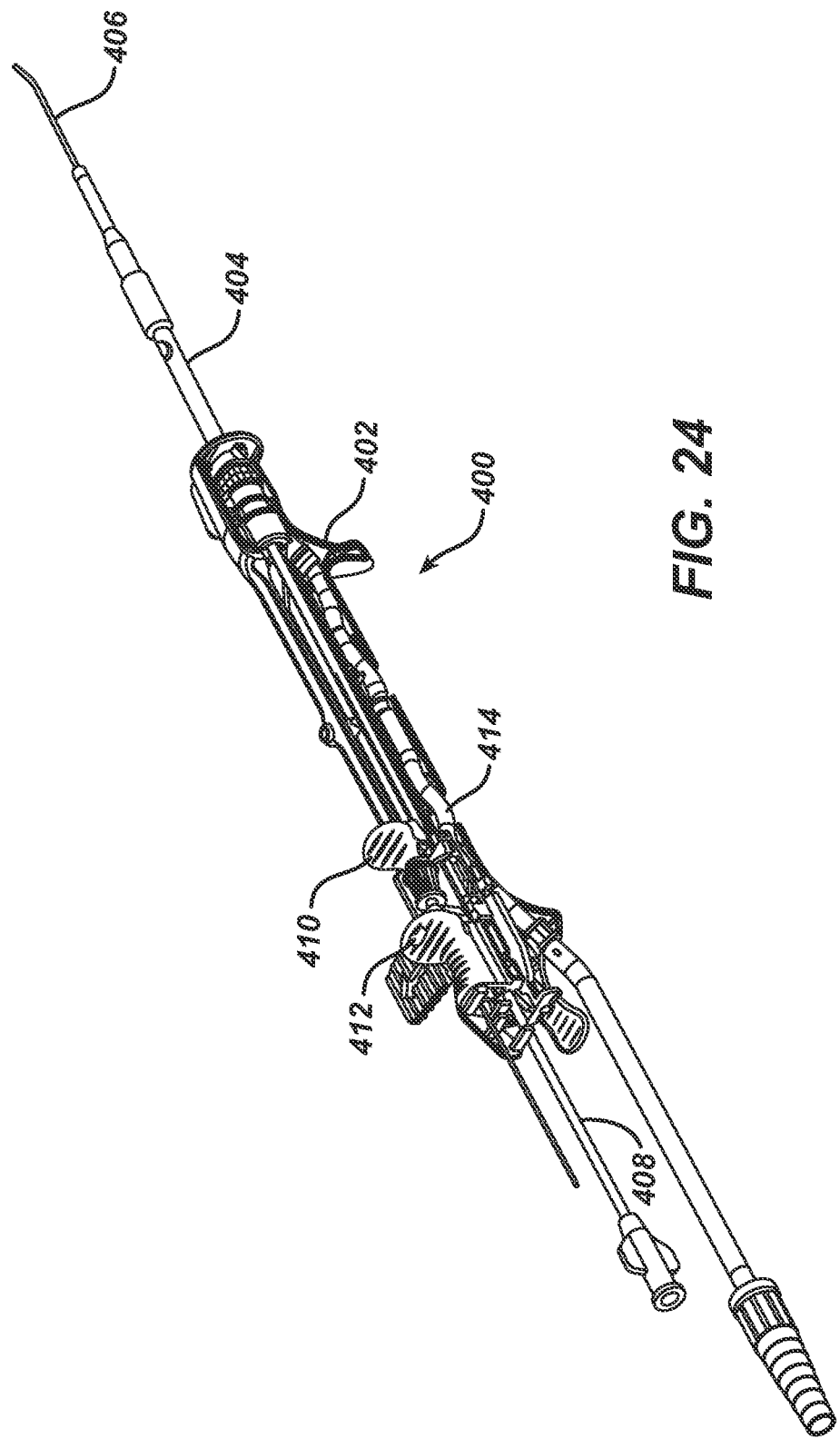
FIG. 24 is a cross-sectional view of a medical device for the treatment of a sinus opening according to an alternative embodiment of the present invention.

FIG. 23 is a flow diagram depicting stages in a method 300 for treating a sinus opening (such as a Frontal, Maxillary, or Sphenoid sinus opening) according to an embodiment of the present invention. Method 300 includes, at step 305, attaching a guide tip with a predetermined angle to a medical device for the treatment of a sinus opening. The attachment of the guide tip can, if desired, be such that the guide tip has an appropriate orientation to the remainder of the medical device for the sinus opening to be treated. A preferred, but non-limiting, orientation is an orientation wherein the guide wire movement mechanism and balloon catheter movement mechanism of the medical device face the user (for example, a physician) during guide wire and balloon catheter advancement.

The medical device for treatment of a sinus opening is then partially inserted into a patient's anatomy (see step 310 of FIG. 23). In step 310, the medical device is, for example, inserted into a patient's nostril to gain access to the sinus ostia (passage). If desired, the medical device can be rotated up to 180 degrees (depending on sinus type) in either direction about the longitudinal axis of the medical device following insertion.

A guide wire of the medical device is then advanced into the patient's sinus via sliding movement of a guide wire movement mechanism of the medical device along a handle of the medical device, as noted in see step 315 of FIG. 23.

Rotation of the guide wire within the patient's sinus via user operation of an integrated guide wire locking and rotation mechanism of the guide wire movement mechanism (for example, the barrel and collet axle of FIGS. 11 through 14) occurs at step 320. Such rotation can be employed to, for example, obtain access to a sinus opening or during confirmation of such access using an illuminated guide wire.

At step 325, the guide wire advancing and rotating steps (i.e., steps 315 and 320 of FIG. 23) are repeated as appropriate to position the guide wire in the sinus opening to be treated.

Subsequently, at step 330, a balloon catheter of the medical device is advanced along the guide wire via sliding movement of a balloon catheter movement mechanism of the medical device along the handle of the medical device. At step 335, the sinus opening is treated via inflation of the balloon catheter. Following treatment of the sinus opening, the balloon catheter is deflated as recited in step 340 of FIG. 23. The balloon catheter and guide wire are then retracted into the medical device (see step 345) and the medical device removed from the patient's anatomy (see step 350).

Method 300 can, if desired, include an additional step of irrigating the sinus opening using the medical device. For example, following retraction of the balloon catheter and guide wire, the treated sinus opening can be irrigated with the medical device prior to removal of the medical device from the patient's anatomy. Such irrigation can involve, as a non-limiting example, exchanging at least the balloon catheter and guide wire with a suitable irrigation cartridge such that the irrigation cartridge is operatively installed in the medical device. The operative installation of the irrigation cartridge can include, for example, disposing the irrigation cartridge in the medical device such that the irrigation cartridge extends through the guide catheter and into the sinus opening with or without a guide wire. In an alternative embodiment, the irrigation may be accomplished through an irrigation balloon catheter incorporated in the medical device.

An alternative embodiment according to the invention will now be described with regard to FIG. 24 to FIG. 32. An assembled device 400 is shown with a portion of the handle 402 removed so that the device can be described in detail. The medical device 400 for the treatment of a sinus opening includes a guide catheter 404, a guide wire 406, a balloon catheter 408, a guide wire movement mechanism 410, a balloon catheter movement mechanism 412, and a suction pathway 414. Each of the portions of the device 400 is shown in greater detail in FIG. 25 and in FIGS. 26-32. The handle 402 (shown split in two halves 402a and 402b in FIG. 25) is ergonomically designed such that the finger anchoring pegs 416a, 416b and 416c can be placed between the fingers of either a right handed or left handed user to provide for support of the device 400. In a single-handed manner, the user's thumb can then reach the suction port 418 for use of the suction pathway 414 to remove materials from the paranasal sinus or sinus canal, the guide wire movement mechanism 410 for advancement and rotation of the guide wire 406 and the catheter movement mechanism 412 for advancement of the balloon catheter along the properly positioned guide wire 406.

Figure 25:
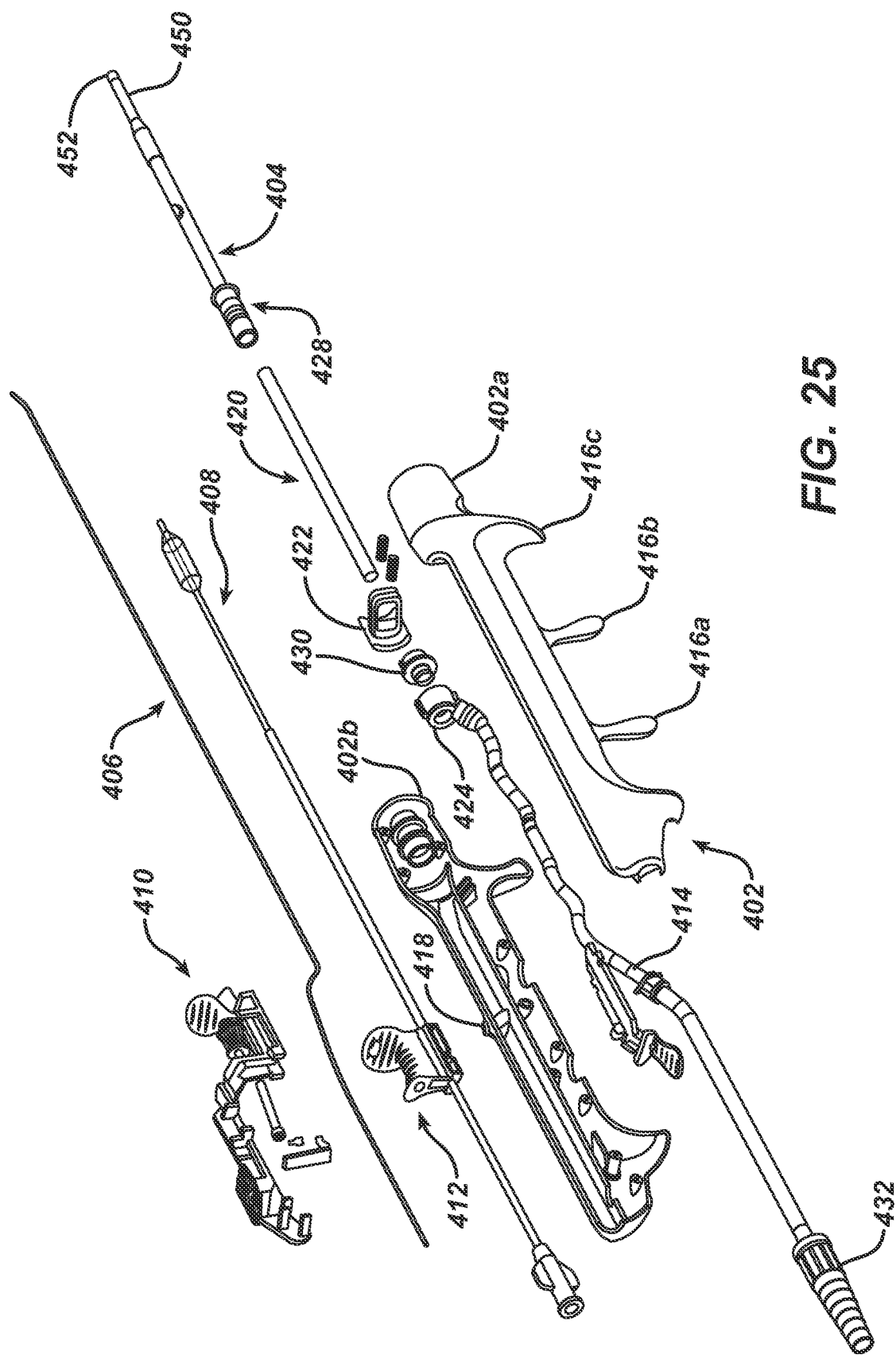
FIG. 25 is a partially exploded view of the device of FIG. 24.
Figure 26A:
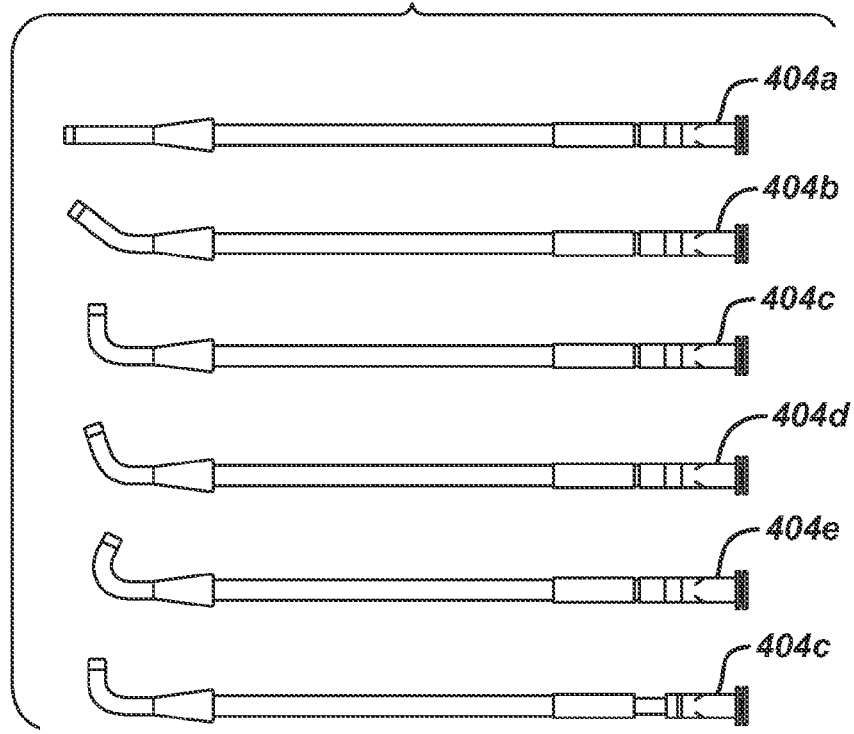
FIG. 26A shows a collection of sinus guide catheters useful for positioning of the sinus balloon catheters of the invention.
Figure 26B:
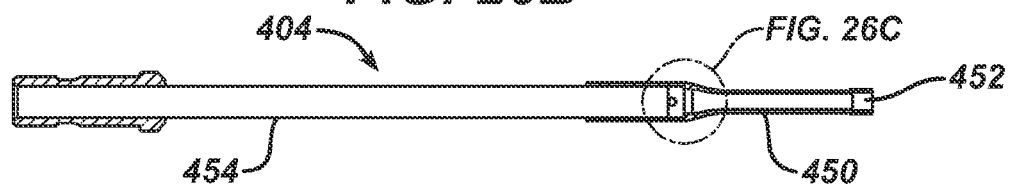
FIGS. 26B and 26C show detailed views of portions of the guide catheters shown in FIG. 26A.
Figure 26C:
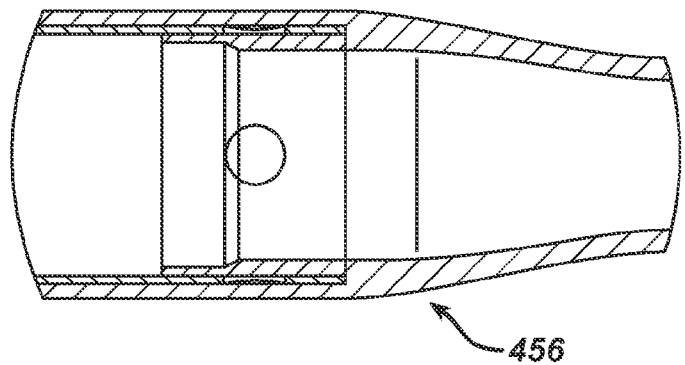
Figure 28:
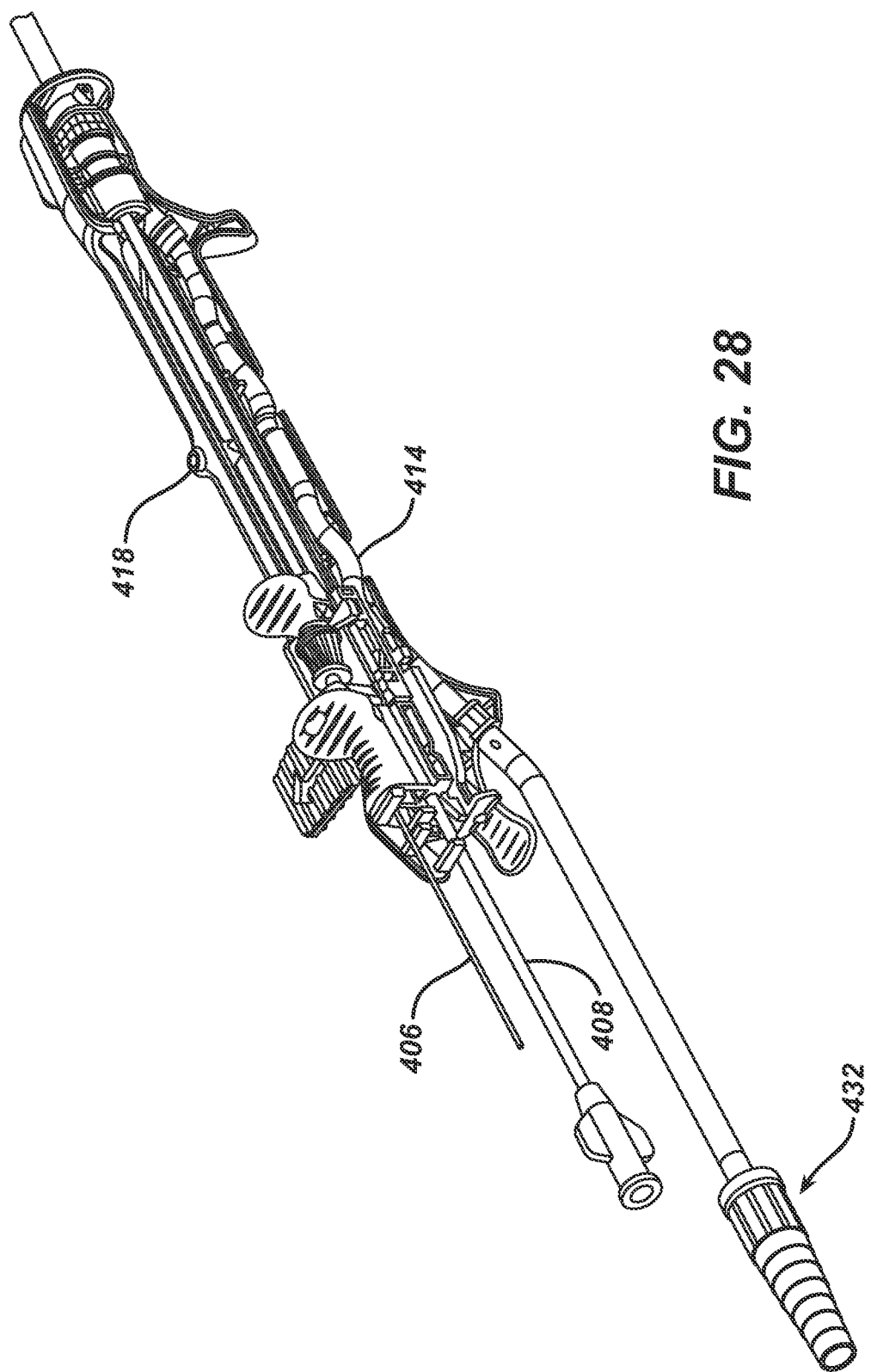
FIG. 28 is an enlarged perspective view of the device of FIG. 24 showing the suction pathway according to the invention.

In the embodiment shown with regard to FIG. 24 to FIG. 32, the representative guide catheter 404 has a linear (0 degree) configuration, but the guide catheter 404 can have any of the configurations shown in FIG. 26A. These guide catheters 404a-404f are substantially rigid and each has a preset distal curve of 0 degrees (404a), 30 degrees (404b), 90 degrees (404d), 70 degrees (404c) or 110 degrees (404e and 404f). Different curvatures are useable to access the ostia of different sinuses as described above with regard to the guide tips 116 of FIG. 8, however the guide catheters 404a-404f described herein do not have detachable tips. For example, a 70 degree guide is typically used to access the ostium of a frontal sinus, a 90 or 110 degree guide is typically used to access the ostium of a maxillary sinus, etc. Each of these guide catheters 404a-404f has a minimum path length (the longitudinal distance through the guide catheter) of 4 cm, a maximum path length of 25 cm, and often a path length of between about 10 and 12 cm. As shown in FIGS. 26B and 26C, each guide catheter 404 has a translucent balloon window 450 and a distal tip 452 that permits endoscopic visualization of the placement of the guide catheter in the sinus anatomy. A rigid distal portion 454 (in this case a stainless steel hypotube, but which could be other similar rigid materials), provides for easy access to the sinus anatomy while the translucent balloon window 450 (in this case a nylon window but which could be other similar transparent materials) provides for easy visualization of the balloon. A soft guide tip 452 (which could include 20% barium sulfate and other similar radiopaque materials) provides for atraumatic, visualizable access to the target sinus.

The guide catheter 404 is connected to handle 402 over sheath 420 by click locking the guide catheter 404 into place over sheath 420 (see FIG. 25). Insertion of the proximal hub 428 of the guide catheter 404 seats the collar 430 of the sheath 420 against the guide catheter lock 424. The button 422 is spring loaded and biases the locked guide catheter proximal hub 428 to reduce radial movement of the guide catheter 404. As can be seen in FIG. 27B, the elastomeric valve 424 further compresses against the proximal hub 428 through collar 430 of the sheath 420 to reduce axial movement of the guide catheter 404. The guide catheter 404 can be positioned in any number of positions, but 8 different positions may be incorporated (in addition to the tip up, tip down, tip right and tip left orientations described in Table 1 above, the orientations can include tip up right, tip up left, tip down right and tip down left, according to the sinus anatomy and the handedness and preference of the user). Once properly positioned, auditory feedback (a click) will ensure proper guide catheter locking. To remove the guide catheter 404 from the handle 402, or to reposition the guide catheter 404, the guide catheter release button 422 is depressed and the guide catheter 404 can be rotated or slide over the sheath 420, removed, and replaced with another guide catheter 404. In an alternative embodiment, the guide catheter (or guide tip described above) can be formed of malleable material that enables the user to configure the shape of the guide catheter prior to inserting the medical device into a patient's anatomy. In this case, the guide catheter can be formed of any suitable malleable material know to one skilled in the art. An exemplary but non-limiting malleable material is heat treated (e.g. annealed) stainless steel. Further, the guide catheter may be steerable such that once in the patient's anatomy, it can alter its shape to conform to the sinus pathway.

Referring again to FIG. 25, in addition to the handle 402, guide catheter 404 and guide catheter lock 424, the suction pathway 414 allows for suction of blood or other matter from the sinus cavity. As shown in greater detail in FIG. 28, suction luer 432 can be attached to an appropriate source of suction and the sinus cavity can be suctioned through the guide catheter 404 and the suction pathway 414, while covering the suction port 418 with the thumb to increase the strength of suction through the pathway.

Figure 29:
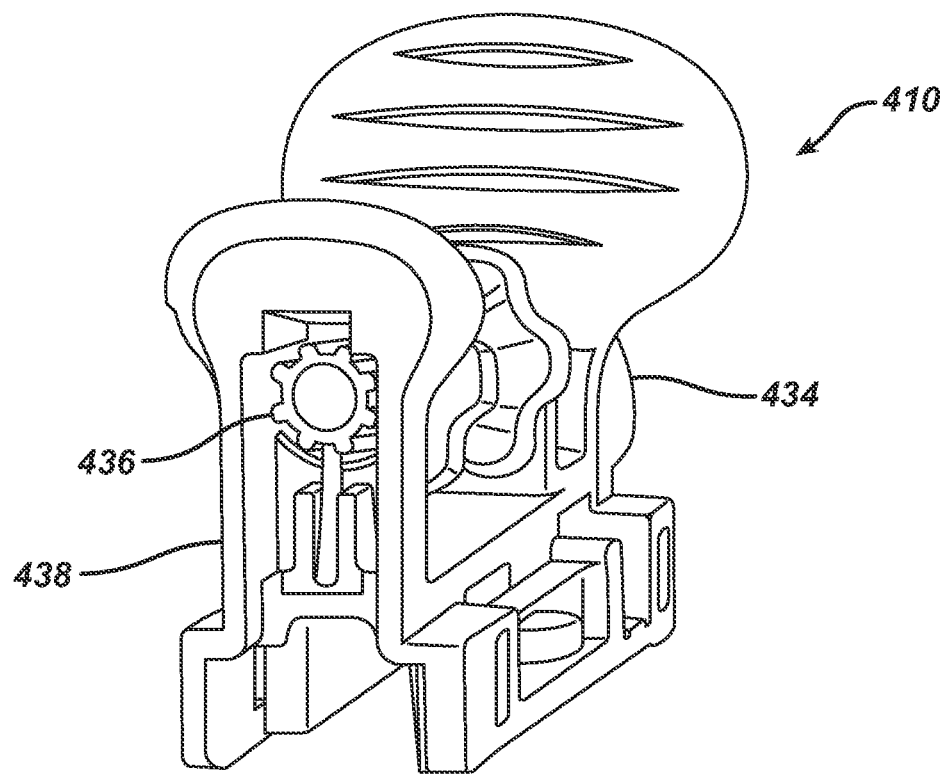
FIG. 29 is an enlarged perspective view of the guide wire actuator of the device of FIG. 24.

Further shown in FIG. 25 are the balloon catheter 408 and balloon catheter movement mechanism 412 and the guide wire 406 and guide wire movement mechanism 410. The guide wire movement mechanism 410 is shown in detail in FIG. 29 and allows for advancing, retracting and rotating the guide wire 406. The mechanism 410 integrates a guide wire locking and rotation mechanism 434 configured for rotation of the guide wire 406 and for securely locking and unlocking the guide wire 406 to the guide wire movement mechanism 410 as further described with regard to guide wire locking and rotation mechanism 240 above. Included in FIG. 29 is clicker 438, a flexible material, in this case a flexible strip, that interacts with the fins of collet 436 to provide audible and tactile feedback of rotation of the locking and rotation mechanism 434 and the resultant rotation of the guide wire 406. A representative guide wire 406 incorporated in the device 400 of the invention is the Relieva Luma Sentry™ Sinus Illumination System manufactured by Acclarent, Inc., Menlo Park, Calif., a guide wire system that can be connected to a light source for illumination and subsequent transcutaneous visualization of the sinus cavity.

The balloon catheter 408, balloon catheter movement mechanism 412, and the balloon catheter shaft 460 are shown in detail in FIGS. 30A, 30B, and 30C. FIG. 30A shows the balloon catheter shaft 460 from above with the dilation balloon 462 on the distal portion 464 of the shaft 460 and an inflation luer 466 at the proximal portion 468 of the shaft. As shown in FIG. 30B, between the balloon catheter movement mechanism and the mid-catheter joint 470 shown in FIG. 30C, the catheter shaft 460 comprises a shaft rail 472 (in this case constructed of a 304 stainless steel hypotube with an inner polymeric sleeve, but which may be any similar materials). The shaft rail 472 has a slit 474 (an opening in the hypotube and a cut in the sleeve) that allows for passage of the guide wire 406 from the balloon guide wire movement mechanism 412 and into the guide wire lumen 476 of the balloon catheter. The rail 472 and slit 474 allow for easy movement of the guide wire 406 while preventing its buckling. As described above with regard to FIG. 10, the mid-catheter joint 470 of the balloon catheter shaft 460 transitions from a balloon catheter shaft 460 with a single inflation lumen 478 at its proximal portion 480 to a middle section 482 dual lumen portion that consists of a guide wire lumen 476 and an inflation lumen 478 and finally to a distal portion 484 of the balloon catheter shaft 460 with a coaxial lumen 486 that has an inner guide wire lumen 488 and an outer inflation lumen 490. Both the guide wire lumen and the balloon catheter lumen proximal to the mid-catheter joint are constructed of a stainless steel hypotube. In the proximal section 480 the inflation lumen 478 is round in cross-section, in the middle section 482 the inflation lumen 492 is oval in cross-section (it is below the guide wire lumen), and the inflation lumen transitions to a coaxial configuration.

Figure 31A:
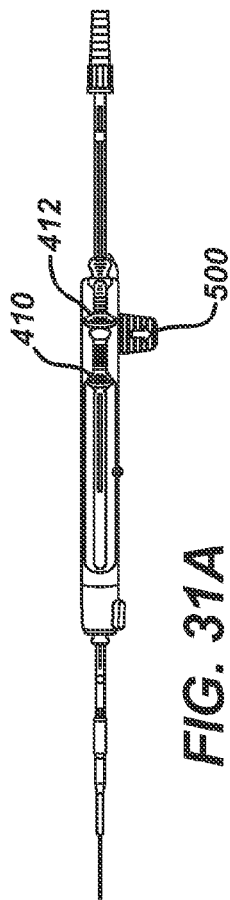
FIGS. 31A, 31B and 31C are top views of the device of FIG. 24 showing a guide wire lock mechanism according to the invention.
Figure 31B:
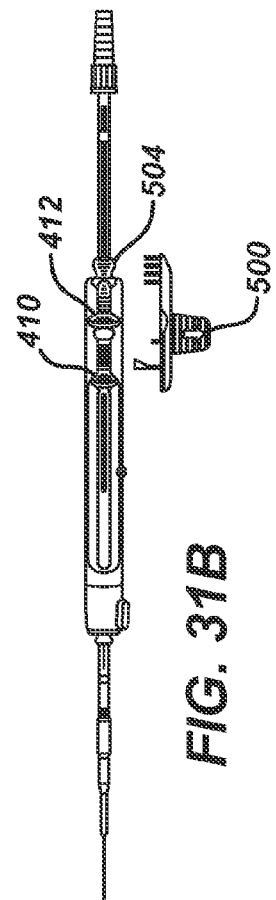
Figure 31C:
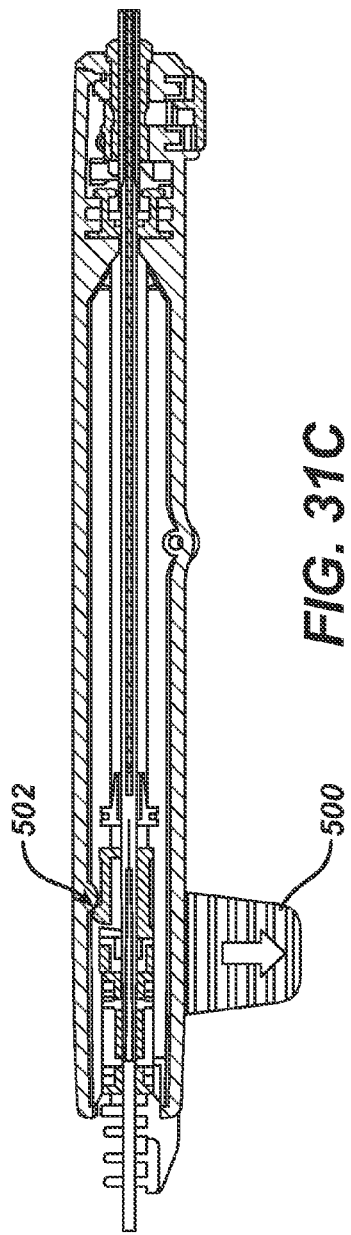
Figure 31D:
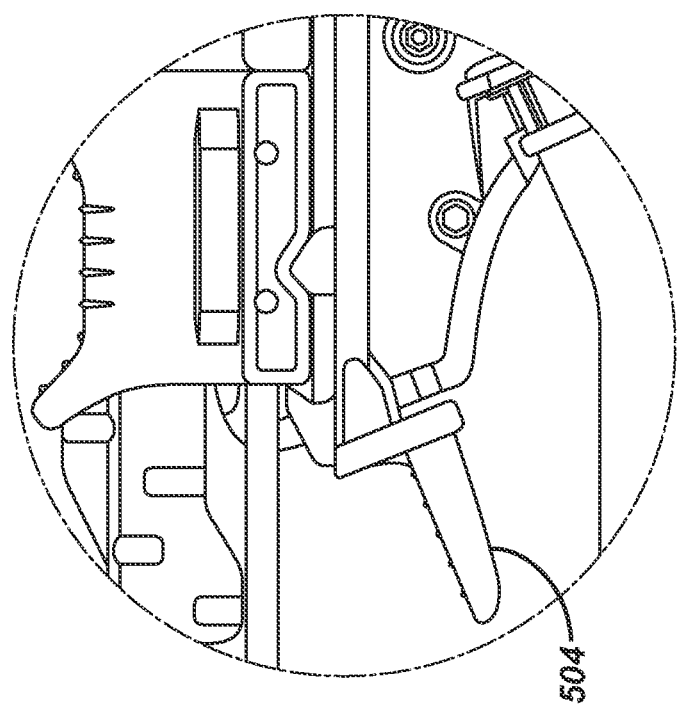
FIG. 31D is a side view of the locking tab of the device of FIG. 24 for securing the balloon catheter actuator according to the invention.
Figure 32:
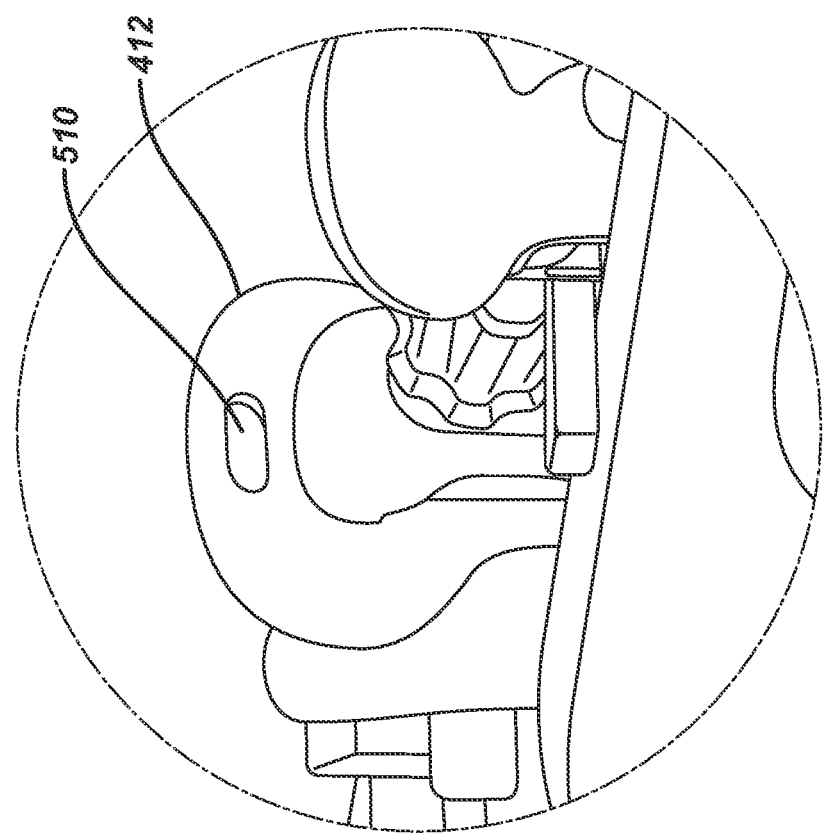
FIG. 32 is a perspective view of the balloon catheter actuator of the device of FIG. 24 for guide wire manipulation without the wire actuator according to an alternative embodiment of the invention.

Prior to operation of the device, the guide wire movement mechanism 410 and the balloon catheter movement mechanism 412 are locked in place as shown FIGS. 31A and 31B. The guide wire lock 500 connects the guide wire movement mechanism 410 and the balloon catheter mechanism 412 and holds the wire 206 stationary, preventing inadvertent movement of the guide wire 206, which prevents the wire from slipping when the barrel 246 is unlocked (see FIG. 13). Once the guide wire lock 500 is removed, the guide wire movement mechanism 410 can be moved independently down the shaft rail 472. The detent 502 prevents inadvertent movement of the guide wire 406 unless the guide wire movement mechanism 410 is moved or unless the guide wire movement mechanism is bypassed. As shown in FIG. 32, where desired at the preference of the user, the guide wire 406 can be manipulated by the user without the use of the guide wire movement mechanism 410 by removing the guide wire 406 from the balloon catheter movement mechanism 412 and the guide wire movement mechanism 410 and threading the guide wire 406 through the opening 510 in the balloon catheter mechanism 412 and over the guide wire movement mechanism 410, effectively bypassing it.

The spring-loaded locking tab 504 prevents the balloon catheter mechanism 412 from moving proximally when it is in the up position, but allows for movement distally (see FIG. 31D) when activated by the thumb or finger. When the locking tab 504 is in the down position, the balloon catheter 408 and guide wire 406 can be removed such that an irrigation catheter can be inserted into the handle 402 and through the guide catheter 404.

Once apprised of the present disclosure, one skilled in the art will recognize that methods according to embodiments of the present invention including method 300 can be readily modified to incorporate any of the techniques, benefits and characteristics of medical devices according to embodiments of the present invention and described herein. Moreover, one skilled in the art will also recognize that methods according to embodiments of the present invention, including method 300, can be modified to incorporate suitable sinus opening treatment techniques and steps known to one skilled in the art including suitable techniques and steps described in U.S. Pat. Nos. 7,462,175, 7,500,971 and 7,645,272, and U.S. Patent Application Publications 2008/0097154, and 2008/0281156, each of which is hereby incorporated in full by reference. Further, the device and methods according to the present invention may be used, in addition to the treatment of the nasal anatomy, for the treatment or an opening or passageway into the paranasal sinus ostium, a paranasal sinus or a Eustachian tube opening.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that devices and methods within the scope of these claims and their equivalents be covered thereby.

What is claimed is:

1. A medical device for the treatment of a sinus opening, the medical device comprising:
   a handle with:
   a proximal end;
   a distal end; and
   a longitudinal axis along the length of the handle;
   a guide wire;
   a guide catheter attached to the distal end of the handle, the guide catheter having a guide catheter lumen;
   a guide wire movement mechanism operatively disposed on the handle;
   a balloon catheter;
   and
   a balloon catheter movement mechanism operatively disposed on the handle;
   wherein the handle and the guide catheter lumen are configured for operatively accepting the guide wire and the balloon catheter; and
   wherein the guide wire movement mechanism is configured for advancement and retraction of the guide wire disposed at least partially in the handle and the guide catheter lumen through the handle and the guide catheter lumen by user operation of the guide wire movement mechanism; and
   wherein the guide wire movement mechanism includes an integrated guide wire locking and rotation mechanism configured for rotation of the guide wire by rotation of the guide wire locking and rotation mechanism relative to the guide wire movement mechanism and the handle, and for securely locking and unlocking the guide wire to the guide wire movement mechanism; and
   wherein the guide wire movement mechanism comprises a proximal end and a distal end and a longitudinal axis between the proximal end and the distal end, said guide wire movement mechanism configured to direct the guide wire along the longitudinal axis of guide wire movement mechanism from the proximal end to the distal end of the guide wire movement mechanism and in a direction that is not along the longitudinal axis into the handle distal to the distal end of the guide wire movement mechanism; and
   wherein the balloon catheter movement mechanism is configured for advancement and retraction of the balloon catheter disposed at least partially in the handle and in the guide catheter lumen through the handle and guide catheter lumen by user operation of the balloon catheter movement mechanism.

2. The medical device of claim 1 wherein the balloon catheter movement mechanism is configured for advancement and retraction of the balloon catheter through the handle and catheter lumen by user operation of the balloon catheter movement mechanism involving translation of the balloon catheter movement mechanism relative to the handle.

3. The medical device of claim 2 wherein the balloon catheter movement mechanism is configured for advancement and retraction of the balloon catheter through the handle and catheter lumen by user operation of the balloon catheter movement mechanism involving longitudinal sliding of the balloon catheter movement mechanism along the handle.

4. The medical device of claim 1 wherein the balloon catheter movement mechanism is configured for advancement and retraction of the balloon catheter through the handle and catheter lumen by user operation of the balloon catheter movement mechanism involving rotation of at least a portion of the balloon catheter movement mechanism.

5. The medical device of claim 1 wherein the guide wire movement mechanism is configured for advancement and retraction of the guide wire through the handle and the catheter lumen by user operation of the guide wire movement mechanism involving translation of the guide wire movement mechanism relative to the handle.

6. The medical device of claim 1 wherein the guide wire movement mechanism is configured for advancement and retraction of the guide wire through the handle and the catheter lumen by user operation of the guide wire movement mechanism involving longitudinal sliding of the guide wire movement mechanism along the handle.

7. The medical device of claim 1 wherein the guide catheter is configured for attachment, detachment and reattachment to the handle.

8. The medical device of claim 1 further including a guide tip, and
wherein the guide tip is configured for attachment, detachment and reattachment of the guide tip to the guide catheter.

9. The medical device of claim 8 wherein the guide catheter and the guide tip are configured for attachment, detachment and reattachment of the guide catheter to the handle.

10. The medical device of claim 1 further comprising an irrigation system for irrigating the paranasal sinus or sinus canal.

11. The medical device of claim 1 further comprising a suction pathway for removal of materials from the paranasal sinus or sinus canal.

12. The medical device of claim 1 further including a guide wire support disposed within the handle,
wherein the guide wire is at least partially disposed within the guide wire support; and
wherein the guide wire support is configured to prevent buckling of the guide wire within the handle during advancement of the guide wire through the handle.

13. The medical device of claim 12 wherein the guide wire support is generally cylindrical in shape and includes a slit-shaped opening; and
wherein the slit-shaped opening is configured such that, during advancement of the guide wire, the guide wire enters the guide wire support through the slit-shaped opening.

14. The medical device of claim 1 wherein the guide wire locking and rotation mechanism includes:
a barrel with an axial opening therethrough; and
a collet axle at least partially disposed within the axial opening of the barrel.

15. The medical device of claim 1 wherein the guide wire movement mechanism further includes at least one rail configured for sliding movement of the guide wire mechanism along a length of the handle during advancement and retraction of the guide wire.

16. The medical device of claim 1 wherein the balloon catheter movement mechanism further includes at least one rail configured for sliding movement of the balloon catheter mechanism along a length of the handle during advancement and retraction of the balloon catheter.

17. The medical device of claim 1 wherein the guide wire movement mechanism and the balloon catheter movement mechanism are disposed on the handle in a configuration for single-handed operation of both the guide wire movement mechanism and the balloon catheter movement mechanism by a user.

18. The medical device of claim 17 wherein the guide wire movement mechanism and the balloon catheter movement mechanism are disposed on the handle in an in-line configuration along the length of the handle.

19. The medical device of claim 1 wherein the sinus opening is at least one of a Frontal sinus opening, Maxillary sinus opening, and Sphenoid sinus opening.

20. The medical device of claim 1 wherein the guide wire locking and rotation mechanism is configured for thumb-operated rotation of the guide wire.

21. The medical device of claim 1 wherein the guide wire locking and rotation mechanism is configured for single finger operated rotation of the guide wire.

22. The device of claim 1 wherein the guide wire is an illuminating guide wire.

* * * * *